(12) United States Patent
Yang

(10) Patent No.: US 7,466,149 B1
(45) Date of Patent: *Dec. 16, 2008

(54) ELECTRONIC SYSTEM AND SOFTWARE FOR MULTIELECTRODE SENSORS AND ELECTROCHEMICAL DEVICES

(75) Inventor: Xiaodong Sun Yang, San Antonio, TX (US)

(73) Assignee: Corr Instruments, LLC., San Antonio, TX (US)

( * ) Notice: Subject to any disclaimer, the term of this patent is extended or adjusted under 35 U.S.C. 154(b) by 56 days.

This patent is subject to a terminal disclaimer.

(21) Appl. No.: 11/145,849

(22) Filed: Jun. 6, 2005

Related U.S. Application Data

(60) Provisional application No. 60/577,611, filed on Jun. 7, 2004.

(51) Int. Cl.
*G01R 27/08* (2006.01)
*G01N 17/04* (2006.01)

(52) U.S. Cl. .............. 324/700; 205/775.5; 204/404

(58) Field of Classification Search .......... 324/700; 205/775.5
See application file for complete search history.

(56) References Cited

U.S. PATENT DOCUMENTS

| | | | | |
|---|---|---|---|---|
| 2,947,679 A | * | 8/1960 | Marsh et al. | 204/404 |
| 3,259,461 A | * | 7/1966 | Griffin, Jr. et al. | 436/6 |
| 4,349,879 A | * | 9/1982 | Peddie et al. | 700/295 |
| 4,667,150 A | * | 5/1987 | Hausler et al. | 324/700 |
| 5,015,355 A | | 5/1991 | Schiessl | |
| 6,132,593 A | | 10/2000 | Tan | |
| 6,683,463 B2 | | 1/2004 | Yang | |
| 6,690,182 B2 | * | 2/2004 | Kelly et al. | 324/700 |

OTHER PUBLICATIONS

U. Steismo, T. Rogne and J. M. Drugli, "Aspect of Testing and Selecting Stainless Steels for Sea Water Applications," Corrosion/94, Paper No. 492, Houston, TX: NACE International, 1994.

(Continued)

*Primary Examiner*—Vincent Q Nguyen
*Assistant Examiner*—John Zhu

(57) ABSTRACT

An electronic system and software program for multielectrode electrochemical devices; a multielectrode sensor for application in environments containing electrochemically active species; and a multielectrode sensor with a built-in removable large electrode. The electronic system has a large electrode connected to the coupling joint through a resistor element to adjust the potential of the multielectrodes. The electronic system, along with the software program, automatically changes the values of the coupling resistors so that the potentials of a group of electrodes or all the electrodes of a sensor are similar, or automatically disconnects malfunctioning electrodes from the coupling joints to avoid the effect of such electrodes. A variation of the electronic system uses an ammeter or a zero-resistance-ammeter to measure the coupling currents and has resistors between the electrodes and the coupling joint to reduce the transient current produced during switching. The software program also keeps track of the cumulative charge for each electrodes of the multielectrode device so that the cumulative corrosion depth or electrodeposition thickness can be calculated based on the cumulative charge from each electrode. The multielectrode sensor for applications in an environment that contains electrochemically active species has a dual-sensor design, which allows the removal of the signals due to the reactions of the electrochemically active species.

10 Claims, 22 Drawing Sheets

To Electrodes 1 through m of a Multielectrode Device

OTHER PUBLICATIONS

Y.J. Tan, "A New Crevice Corrosion Testing Method and its Use in the Investigation of Oil Stain," Corrosion, vol. 50, No. 4, pp. 266-269, 1994.

Z. Fei, R.G. Kelley and J.L. Hudson, "Spatiotemporal Patterns on Electrode Arrays," Journal of Phys. Chem., vol. 100, No. 49, pp. 18986-18991, 1996.

Y.J. Tan, "Monitoring Localized Corrosion Processes and Estimating Localized Corrosion Rates Using a Wire-beam Electrode," Corrosion, vol. 54, No. 5, pp. 403-413, 1998.

L. Yang et al. "An in-situ Galvanically Coupled Multielectrode Array Sensor for Localized Corrosion," Corrosion, vol. 58, No. 12, pp. 1004-1014, 2002.

L. Yang and N. Sridhar, "Coupled Multielectrode Online Corrosion Sensor," Materials Performance, vol. 42, No. 9, pp. 48-52, 2003.

H. Eren, et al., "An Auto-Switch for Multisampling of a Wire Beam Electrode Corrosion Monitoring System," IEEE Transactions on Instrumentation and Measurement, vol. 47, No. 5, pp. 1096-1101, 1998.

* cited by examiner

| Sensor ID | Ch Bank | Unit | Pin# 1 | Pin# 2 | Pin# 3 | Pin# 4 | Pin# 5 | Pin# 6 | Pin# 7 | Pin# 8 | Pin# 9 | Min | Max | Mean | Icor(nA) | GR(um/y) | Potential (mV) |
|---|---|---|---|---|---|---|---|---|---|---|---|---|---|---|---|---|---|
| 1 | A | (nA) | -1.12E-2 | 1.36E-3 | 1.23E-3 | -1.40E-2 | -1.97E-3 | -2.77E-3 | 1.16E-2 | -3.11E-3 | | | | | | | |
| 1 | B | (nA) | -1.41E-2 | -1.85E-2 | -3.89E-3 | -9.66E-3 | 1.53E-2 | -2.14E-2 | -2.66E-2 | -1.64E-2 | | -3.59E-2 | 1.16E-2 | -1.11E-2 | 4.07E-2 | 2.67E-2 | -166.46 |
| 2 | C | (nA) | -1.96E-2 | -3.07E-2 | -3.15E-2 | -1.92E-3 | 3.63E-4 | -3.20E-3 | -9.66E-3 | 7.78E-3 | -1.43E-2 | | | | | | |
| 3 | D | (nA) | 8.67E-3 | -1.59E-2 | 1.38E-2 | 1.05E-2 | -1.38E-2 | -2.03E-3 | 7.33E-3 | | | -3.16E-2 | 1.38E-2 | -5.97E-3 | 4.13E-2 | 2.70E-2 | -107.85 |
| 3 | E | (nA) | 3.58E-4 | 2.78E-3 | -4.13E-3 | 2.94E-3 | 1.48E-3 | 1.67E-3 | -4.41E-3 | 4.94E-4 | | | | | | | |
| 3 | F | (nA) | 6.77E-3 | -1.09E-3 | -4.88E-3 | -3.33E-3 | -1.22E-2 | 2.06E-3 | 8.93E-3 | -1.05E-2 | | -1.22E-2 | 2.78E-3 | 1.67E-3 | 2.41E-2 | 1.58E-2 | -29.20 |

FIG. 17

ELECTRONIC SYSTEM AND SOFTWARE FOR MULTIELECTRODE SENSORS AND ELECTROCHEMICAL DEVICES

CROSS REFERENCE TO RELATED APPLICATIONS

This application claims the benefit of provisional patent application Ser. No. 60/577,611, filed 2004 Jun. 7 by the present inventor.

BACKGROUND

1. Field of Invention

This invention relates to multielectrode sensors and electronic systems and software for multielectrode sensors and other electrochemical multielectrode devices.

2. Background

Multielectrode array sensors (see U.S. Pat. Nos. 6,683,463 and No 6,132,593) have been used for corrosion monitoring and electrochemical studies [L. Yang and N. Sridhar, "Coupled Multielectrode Online Corrosion Sensor", Materials Performance, 2003, September issue, page 48]. U.S. Pat. No. 6,683,463, to Yang and Sridhar (2004), disclosed a coupled multielectrode sensor system in which each electrode is connected to a common joint through a resistor, and a multichannel high-precision voltmeter is used to scan the potential drop across each resistor to obtain the current flowing though the resistor. However, the use of a single resistor for each electrode of the sensor limits the range of corrosion rates in which the sensor effectively simulates the one-piece-metal behavior because the one-piece-metal concept requires that the potentials of all the electrodes of the sensor are essentially the same. In addition, no current software allows the flexible configuration of the multiple electrodes during the measurements. This invention is related to several electronic systems and sensor designs, and a user-friendly software program for monitoring corrosion or studying electrochemical processes using the concept of multielectrode sensors or electrochemical devices.

The inventor has recently filed a patent application related to the instrument and user-friendly software, titled "An Electronic System and Software for Multielectrode Sensors and Electrochemical Devices." In that patent application, a basic electronic unit, an integrated electronic system, and the associated software program for coupled multielectrode electrochemical devices or sensors were disclosed. The basic electronic unit uses different values of resistors for coupling the multiple electrodes in a sensor, so that the effective value of the coupling resistance can be dynamically changed according to the magnitude of the measured coupling current during the measurement. This feature allows the electronic unit to measure a wide range of coupling currents, without compromising the principle that the coupled electrochemical device simulates the one-piece-metal behavior. The integrated electronic system uses several basic electronic units, so that it can simultaneously measure several independent multielectrode electrochemical devices or sensors that have a small number of electrodes, or measure one or more multielectrode devices or sensors that have a large number of electrodes. The software gives users the ability to change the data acquisition parameters dynamically during the measurements.

The present patent application is an improvement of the previously filed patent application. Some of the improved features by the present invention include:

An electronic system that has a large electrode connected to the coupling joint through a resistor element, to adjust the potential of the electrodes.

An electronic system and software program that automatically change the values of the coupling resistors, so that the potentials of a group of electrodes or the entire electrodes of a sensor are similar, or automatically disconnect malfunctioning electrodes from the coupling joints to avoid the effect by such electrodes.

An electronic system that uses an ammeter or a zero-resistance-ammeter to measure the coupling currents and has resistors between the electrodes and the coupling joint, to reduce the transient current produced during switching.

A software program that also keeps track of the cumulative charge for each electrode of the multielectrode device, so that the cumulative corrosion depth or electrodeposition thickness can be calculated based on the cumulative charge from each electrode.

A multielectrode sensor system with a dual-sensor design that allows it to be used in systems containing electrochemically active species.

BRIEF DESCRIPTION OF DRAWINGS

FIG. 10 shows a software interface for setting up the connections between the multielectrode device or sensors and the connector banks on the instrument panel.

FIG. 11 is a variation of the specifications for the software interface for setting up the connections between the multielectrode device or sensors and the connector banks on the instrument panel.

FIG. 17 shows a software interface for measurement with the dynamically displayed current from each electrode and the statistical parameters, numerical values of corrosion current and corrosion rate, and corrosion potential for each sensor.

Figure 1:
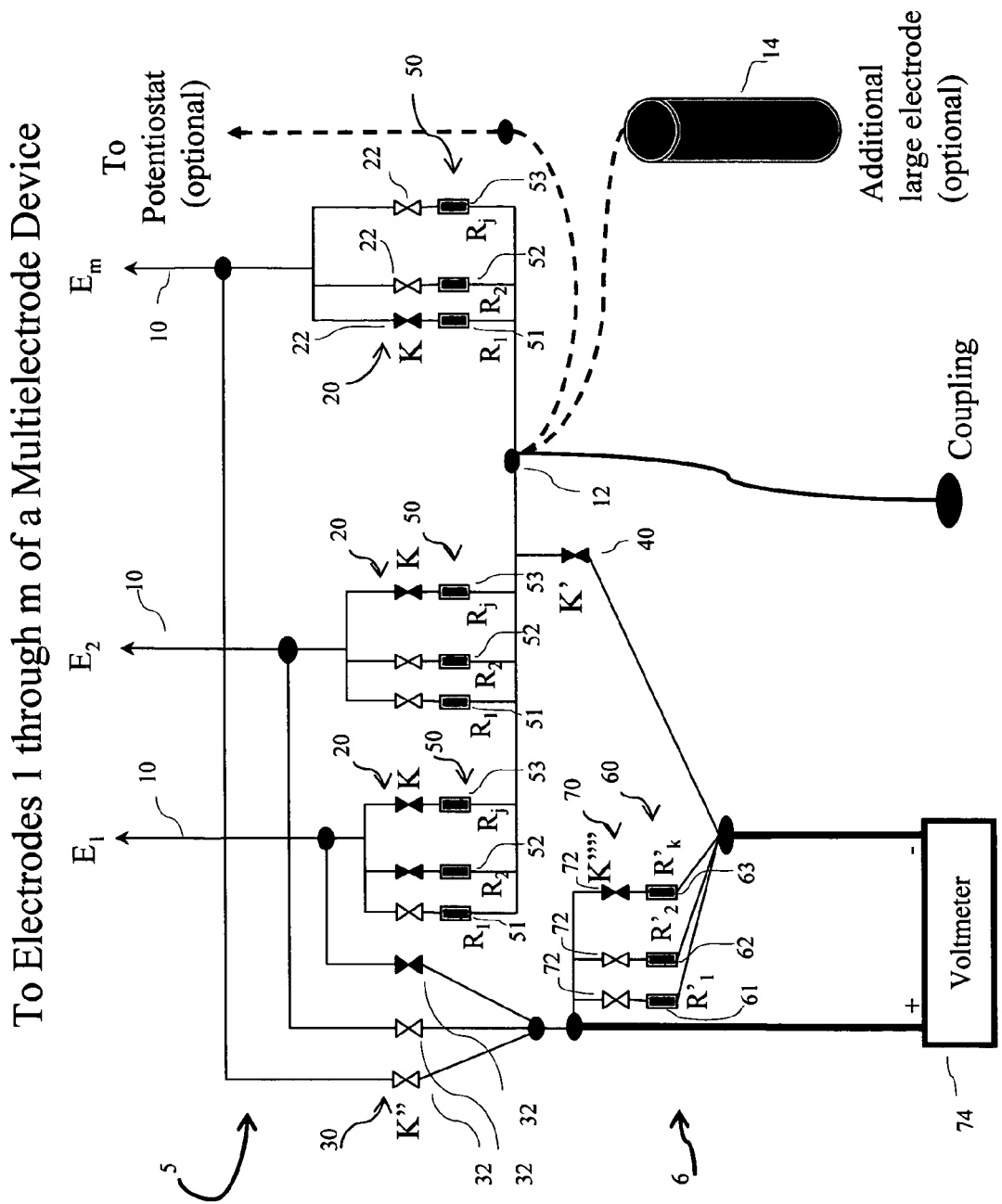
FIG. 1 is a schematic diagram of a basic electronic unit for using a voltmeter to measure the coupling current from each electrode.

| REFERENCE NUMBERS OF DRAWINGS | |
|---|---|
| 5 | basic electronic unit |
| 5a | basic electronic unit for working sensor |
| 5b | basic electronic unit for baseline sensor |
| 6 | voltage-measuring unit |
| 10 | electrode wires from a basic electronic unit for connection to the first through the last electrodes of a multielectrode device or a group of electrodes of a multielectrode device |
| 12 | coupling joint of a basic electronic unit |
| 14 | large electrode |
| 20 | group of auto switches that are connected to each electrode in parallel (called K switches) |
| 22 | K switches (filled symbols indicate closed state and open symbols indicate open state) |
| 30 | group of auto switches connecting each electrode to a voltmeter or an ammeter (called K" switches) |
| 32 | K" switches (filled symbols indicate closed state, and open symbols indicate open state) |
| 40 | auto switch connecting the coupling joint to the voltmeter (called K' switch; filled symbols indicate closed state, and open symbols indicate open state) |
| 50 | group of resistors that are between each electrode and the coupling joint (R group resistors) |
| 51 | R resistor #1 ($R_1$) with the lowest resistance value |
| 52 | R resistor #2 ($R_2$) with a higher resistance value |
| 53 | R resistor #j ($R_j$) with the highest resistance value |
| 60 | a group of resistors in the voltage-measuring unit that are in parallel with the R group resistors (called R' group resistors) |
| 61 | R' resistor #1 ($R'_1$) with the lowest resistance value |
| 62 | R' resistor #2 ($R'_2$) with a higher resistance value |
| 63 | R' resistor #j ($R'_j$) with the highest resistance value |
| 70 | group of auto switches that close or open the R' resistors (called K"" switches) |
| 72 | K"" switches (filled symbols indicate closed state, and open symbols indicate open state) |
| 74 | voltmeter |
| 76 | ammeter or zero-resistance ammeter |
| 80 | auto switches that connect between the coupling joints of any two or more basic electronic units (called K''' switches) |
| 81 | switch for measurement of the potential of the coupling joint against a reference electrode with the voltmeter (called $K^7$ switch) |
| 82 | reference electrode |
| 83 | cathode |

-continued

| REFERENCE NUMBERS OF DRAWINGS | |
|---|---|
| 84 | power source |
| 85 | group of resistors that are between the coupling joint and the cathode ($R''_1 < R''_2 < \ldots < R''_p$) |
| 86 | auto switches that close or open the R" resistors (they are called $K^5$ switches here; filled symbols indicate closed state, and open symbols indicate open state) |
| 87 | switch that connects the reference electrode to the input of the voltmeter (called $K^6$ switch) |
| 88 | switch that connects the wire from the K" switch to a voltmeter (called $K^9$ switch) |
| 89 | switch that connects the wire from the K" switch to an ammeter (called $K^8$ switch) |
| 90 | instrument panel |
| 91 | electrical connector for basic electronic unit (designated Bank A, B, C, ... for 1st, 2nd, 3rd, ... basic electronic units) |
| 92 | electrical connector for two or more basic electronic units (with more pins) |
| 93 | electrical connector for more basic electronic units (with even more pins) |
| 94 | numerical number showing the number of pins used on connector or available for measurement. |
| 96 | connector connected to the coupling joint of a basic electronic unit (designated as A, B, C, ... for $1^{st}$, $2^{nd}$, $3^{rd}$, ... basic electronic units) |
| 102 | cables that connects a group of wires from each basic electronic unit to the different types of electrical connectors |
| 110 | working sensor in a dual sensor design |
| 112 | baseline sensor in a dual sensor design |
| 120 | combination sensor in a dual sensor design |
| 122 | working sensor electrode in a combination sensor |
| 124 | baseline sensor electrode in a combination sensor |
| 126 | cable connected to working sensor electrodes of a combination sensor |
| 128 | cable connected to baseline sensor electrodes of a combination sensor |
| 130 | sensor body or sensor protection tube |
| 132 | sensing electrodes |
| 134 | insulation |
| 135 | electrical cable |
| 140 | large removable rod-shaped electrode with a female thread at one end |
| 142 | metal connector with a male thread at end for connection to the large removable rod-shaped electrode |
| 144 | large removable tube-shaped electrode with internal thread |
| 146 | external thread on sensor body for attaching large removable tube-shaped electrode and for forming electrical contact between the embedded wire and the electrode |
| 148 | embedded wire for connection to the tube-shaped large removable electrode if body is made of non-conducting material |

DETAILED DESCRIPTIONS AND OPERATIONS

FIGS. 1 through 9—Electronic Hardware

FIG. 1 shows a schematic diagram of a basic electronic circuit 5 for measuring the coupling current from each electrode, by using a voltage-measuring unit 6 that has a voltmeter 74 to measure the potential drop across the R resistors 50 and R' resistors 60. There are j different values of R resistors, 51 ($R_1$), 52 ($R_2$), . . . , and 53 ($R_j$) ($R_1 > R_2 > \ldots > R_j$) connected in parallel between the coupling joint 12 and the electrode wires 10, for connection to each electrode. With this connection, a suitable value of the parallel resister can be automatically selected to couple the electrodes in a multielectrode device or sensor, or in a group of electrodes in a multielectrode device or sensor to one common coupling joint 12. The effective value of the R resistors 50 is such that the voltage across the R resistors 50 is small enough for all the electrodes connected to the electrode wires 10 to simulate the electrochemical behavior of a one-piece metal, and yet significantly higher than the detection limit of the voltmeter 74. The R resistors 50 that are used in the coupling are called the coupling resistors.

The decision regarding which value of R resistor to use for coupling will be determined by a computer or a microprocessor, based on the dynamically measured current from each electrode. The selection of the proper R resistor is achieved by a computer or microprocessor, using the K switches 20 and 22, as shown in FIG. 1. The K switches in FIG. 1 may be replaced with manual switches that are adjusted manually, according to the prompt by the computer or the microprocessor. Use of the K switches allows the electronic circuit to measure a large range of coupling currents with a relatively cheap and low accuracy voltmeter 74. The R resistors 50 and K switches 20 may be considered a resistance-adjustable resistance element.

With the circuit shown in FIG. 1, the coupling resistors for the different electrodes can be the resistors of same value (use the same R for all electrodes), the resistors of different values, or a combination of resistors that have different values. For example, FIG. 1 uses both 52 ($R_2$) and 53 ($R_j$) for electrode #1 ($E_1$), 53 ($R_j$) for electrode #2 ($E_2$), and 51 ($R_1$) for electrode #m ($E_m$) (with $R_1 > R_2 > \ldots > R_j$). This is an example of a case when the current from $E_1$ is the highest, the current from $E_2$ is lower, and the current from $E_m$ is the lowest. Such a selection of the resistances allows all the voltages across the resistors on the different electrodes to be close to each other, so that the coupled multiple electrodes can better simulate the one-piece-metal behavior.

The K" switches 30 and 32 are the scanning switches that control which of the electrode wires 10 is connected to the voltmeter 74 during the measurement.

The K' switch 40 is used for isolation of the coupling joint 12 from the voltmeter 74, when no measurement is taken.

The K"" switches 70 and 72 may be used by a processor to control which of the R' resistors 60-61 ($R'_1$), 62 ($R'_2$), ..., 63 ($R'_k$) ($R'_1 > R'_2 > \ldots > R'_k$, $k \geq 1$) to use to make the best measurement. The R' resistors 60 are also called the measuring resistors that can further adjust the potential drop between the electrode wires 10 and the coupling joint 12 during the time the potential drop is measured, so that the electronic unit is suitable for a wide range of current. The R' resistors 60 are used to increase the current range the electronic unit can handle, without the cost of adding more K switches 20 between each electrode wire 10 and the coupling 12.

The optional potentiostat or optional large electrode 14 is used to alter the potential of the coupling joint 12. The optional large electrode 14 may be a cathode that has a higher potential than the sensing electrodes or a large same-metal electrode. A cathode is usually used to raise the potential of the coupling joint 12 and a large same-metal electrode is usually used to stabilize the potential of the coupling joint 12. The large electrode 14 may also be a system component such as the piping of a chemical process, the body of a ship in seawater or the rebar in a concrete structure.

Open circuit potential (uncoupling potential) of each electrode can be measured, by opening all of the K switches 20 to that electrode, all of the K"" switches 70 and the K' switch 40, and connecting the input Low of the voltmeter 74 to a reference electrode (see description for FIG. 3 below). If the option for open circuit potential measurement is required, the number of K switches 20 must be equal to j. If the option for open circuit potential measurement is not required, the number of K switches 20 can be j-1, with one of the coupling resistors 50 connected between the electrode wire 10 and the coupling joint 12 directly (without a K switch 20).

When a coupled multielectrode device is used without being connected to the large electrode 14 or to a potentiostat, the sum or mean of the currents from all electrodes of a sensor should be zero. A non-zero mean value represents an error in the system and can be corrected by the software (see the software section). When a coupled multielectrode device is used with a large electrode, the sum or mean of the currents from all electrodes of a sensor may not be zero.

The K switches 20 can also be used to disconnect an electrode from the coupling joint 12 to decouple the electrode, or to use a high effective value of coupling resistor 50 for an electrode, to reduce the degree of the electrode's coupling to the coupling joint 12. This feature is useful when the computer or microprocessor detects that the electrode is having a malfunction. Unless the coupling joint is connected to the large electrode 14 or to a potentiostat, such decoupling or less degree of coupling is important, because the malfunctioning electrode may drive the coupling potential to an extreme and affect the measured signal. An electrode may malfunction if a contaminant that is more active (less corrosion resistant) than the sensing electrodes is attached to the electrode surface. In this case, the malfunctioning electrode may drive the potential of the coupling joint 12 to an un-reasonably low value, if its coupling is not removed or lessened. The computer may detect this kind of malfunctioning electrode according to the following criteria:

1) The out-of-normal signals from the electrode, according to the statistics of the currents measured from all electrodes, and/or 2) Significant non-zero mean current.

If the coupling joint is connected to the large electrode 14 or to a potentiostat, such decoupling may not be necessary, because the potential of the malfunctioning electrode may not change the coupling potential much. However, the signal from the malfunctioning electrode should be excluded in deriving the processed signals, such as the corrosion rate or corrosion penetration depth. If not discarded, the signal from the malfunctioning electrode may significantly affect the processed signals.

Figure 2:
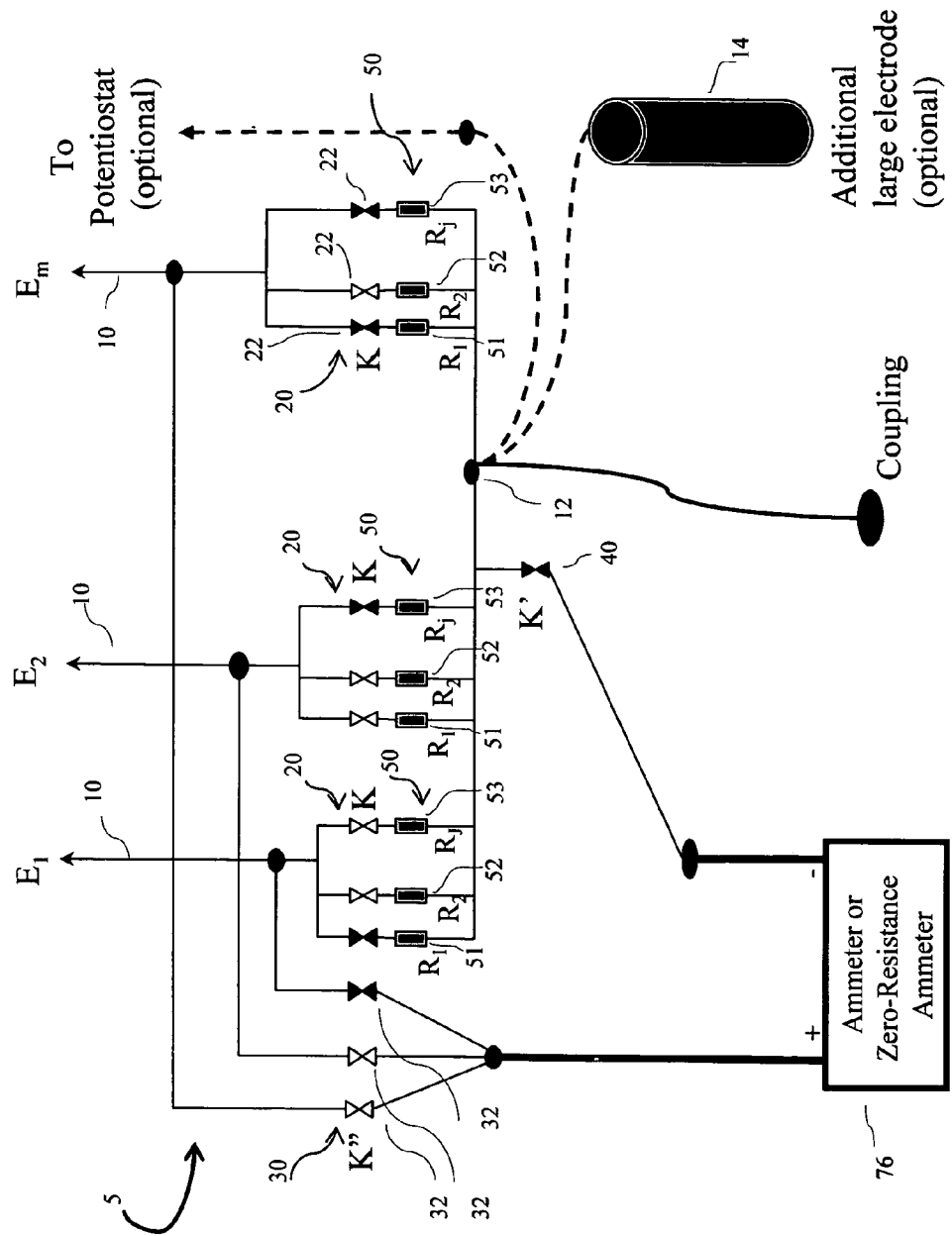
FIG. 2 is a schematic diagram of a basic electronic unit that uses an ammeter or a zero-resistance ammeter to measure the coupling current from each electrode.

FIG. 2 shows that the electronic circuit 5, as shown in FIG. 1, can be used with an ammeter or zero-resistance ammeter 76. In this case, along with the K switches 20, the resistors, whose values are close to the input impedance of the ammeter or the zero-resistance ammeter 76, will be selected during coupling (but decoupled during measurement). The inventor has noticed that a near-zero ammeter (no zero-resistance ammeter has true zero resistance) often could not adequately measure the coupling currents from the electrode wire 10, without inserting a resistor between the electrode wire 10 and the coupling joint 12 shortly before the measurement is taken (before switching on the corresponding K" switch 30). One or more of the resistors may also be used during the measurement of current from an electrode (when the K" switch 30 to this electrode is switched on), to reduce noise spikes that may be experienced with the setup described in U.S. Pat. No. 6,132,593 during switching. In this case, the value of this resistor or the effective value of the group of the parallel resistors 50 must be high enough so that most of the current will flow though the ammeter or zero-resistance ammeter 76.

In the example shown in FIG. 2, resistor 51 ($R_1$) was used during the measurement of the current from $E_1$ to reduce switching spikes (the corresponding K" switch 30 for $E_1$ is on), resistor 53 ($R_j$) was used for coupling of $E_2$, and both resistors 51 ($R_1$) and 53 ($R_j$) were used for the coupling of $E_m$. Other combinations of these resistances can also be used for better performance.

In FIG. 2, the K switch on the largest R resistor 53 ($R_j$) may be replaced by a wire, if this resistor is designed for use during the measurement.

The coupling joint 12 may also be connected to a large electrode or a potentiostat to alter the potential of the coupling joint. The large electrode may also be a system component, such as the piping of a process or the body of a ship.

Figure 3:
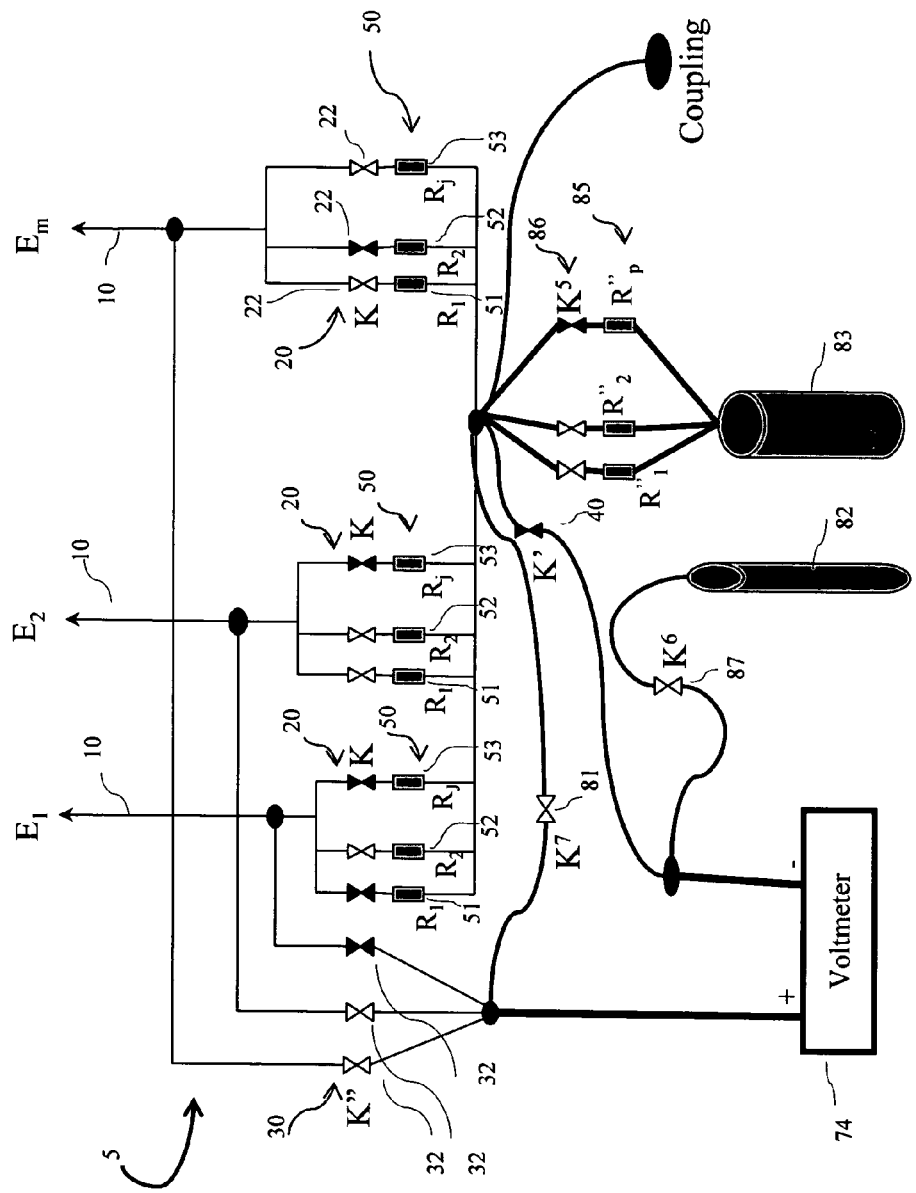
FIG. 3 is a schematic diagram showing the connection of the coupling joint of a multielectrode device to a cathode through a resistor element.

FIG. 3 shows the connection of the coupling joint 12 of a multielectrode device to a cathode 83 using parallel resistors 85 ($R_1''$, $R_2''$, ..., $R_p''$). The parallel resistors 85 and the $K^5$ switches 86 allow a controller to automatically use an optimum value of the effective resistor for galvanic coupling of the coupling joint 12 to the cathode 83, to properly polarize the coupling joint 12. A good polarization criterion is such that the potential at the coupling joint 12 is slightly higher than the highest open circuit potential measured from all the individual electrodes. In this case, the cathode 83 acts as a true cathode for every electrode (and every electrode in the coupled multielectrode device is an anode when the coupling joint 12 is connected to the cathode 83), and yet the coupling potential is not too far from a reasonable value because it is close to the value measured from one of the electrodes, which simulate the metal under corrosion. The cathode 83 may be made of the same material as the electrodes in the multielectrode device, but have a significantly larger surface area than the sensing electrode. The cathode 83 may also be made of a material that is more corrosion resistant than the material of the electrodes in the multielectrode device. The reference electrode 82 is used to measure the open circuit potential of each electrode connected to the electrode wires 10 when both K' switch 40 and $K^7$ switch 81 are open and $K^6$ switch 87 is closed (All K switches 20 must be open, too, see the description section for FIG. 1). The reference electrode 82 is also used to measure the potential of the coupling joint 12 when both K" 30 and K' switch 40 are open, and both $K^7$ switch 81 and $K^6$ switch 87 are closed. The R" resistors 85 and $K^5$ switches 86 may be considered as another resistance-adjustable resistance element.

Figure 4:
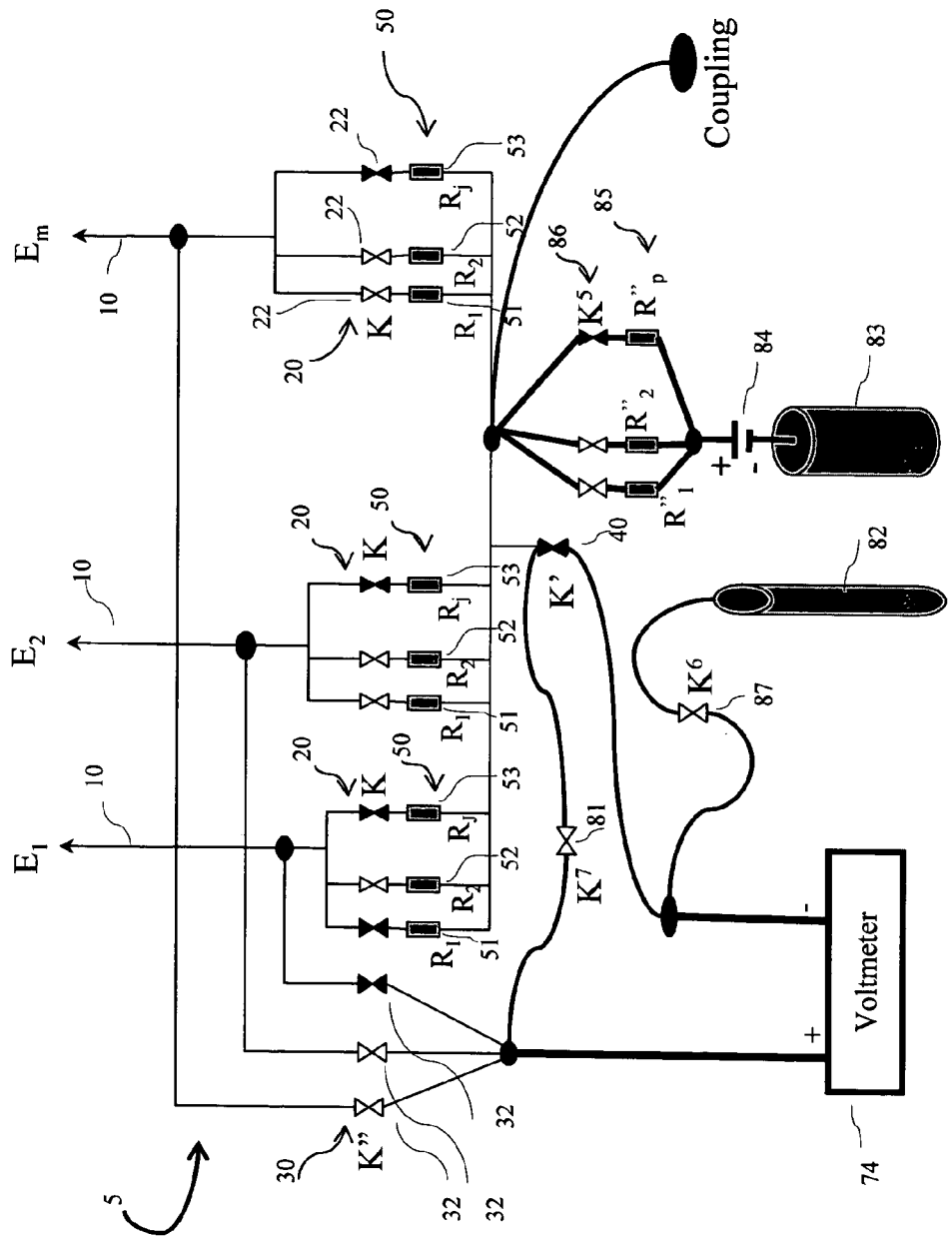
FIG. 4 is a schematic diagram showing the connection of the coupling joint of a multielectrode device to a cathode through a resistor element and a variable power source.

FIG. 4 is a slight variation of FIG. 3. In FIG. 4, a variable power source 84 is connected between the parallel resistors 85 and the cathode 83. Together, the parallel resistors 85, the $K^5$ switches 86, and the variable power source 84 allow a controller to properly polarize the coupling potential, using an optimum resistance (one of R" 85) or a group of resistors (several of R" 85) for galvanic coupling. The power source 84 is especially useful in the case where the potential of the cathode 83 is lower than the potentials of the electrodes.

Figure 5:
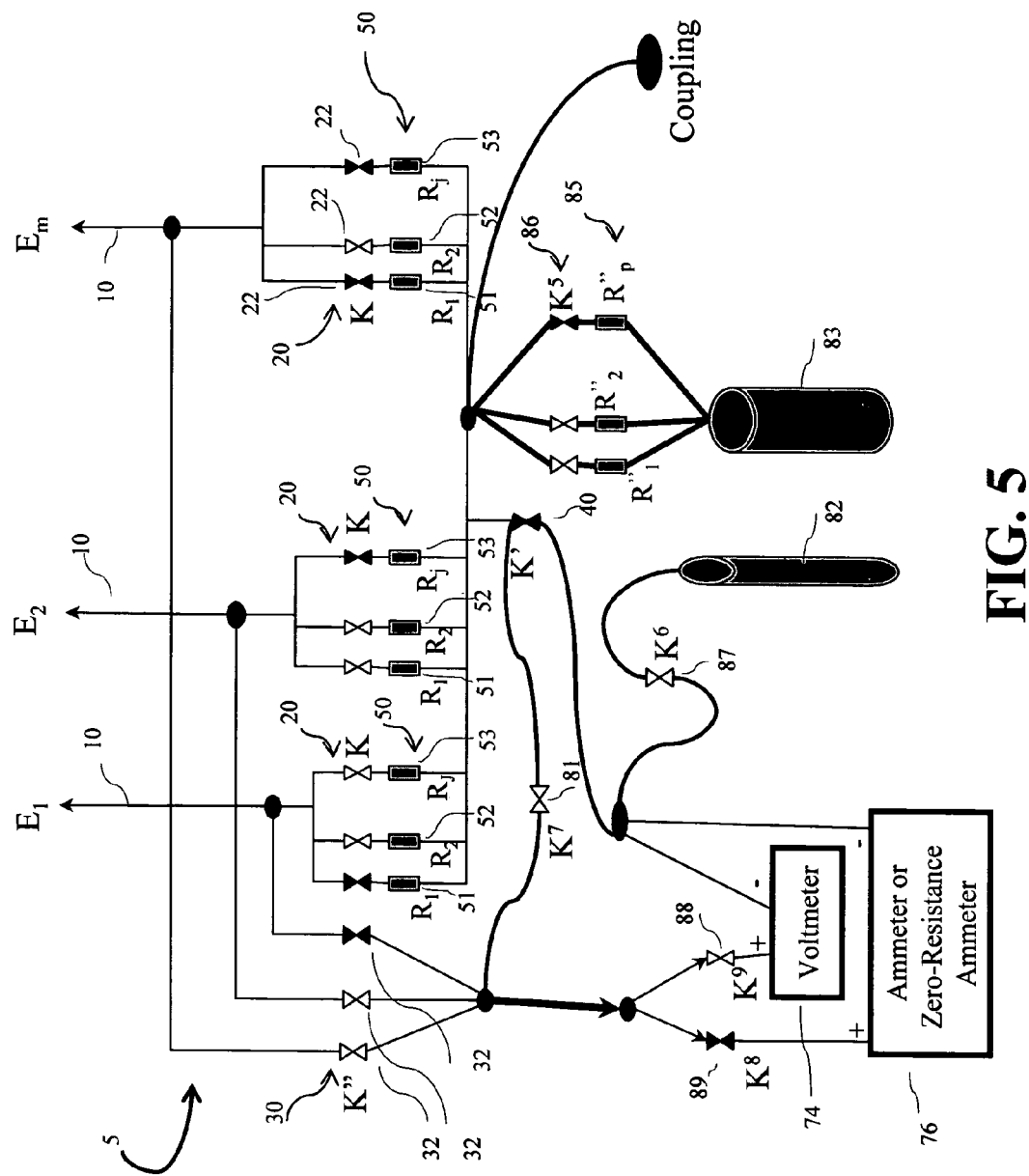
FIG. 5 is a schematic diagram showing the connection of the coupling joint of a multielectrode device to a cathode through a resistor element and an ammeter for the measurement of the currents.
Figure 6:
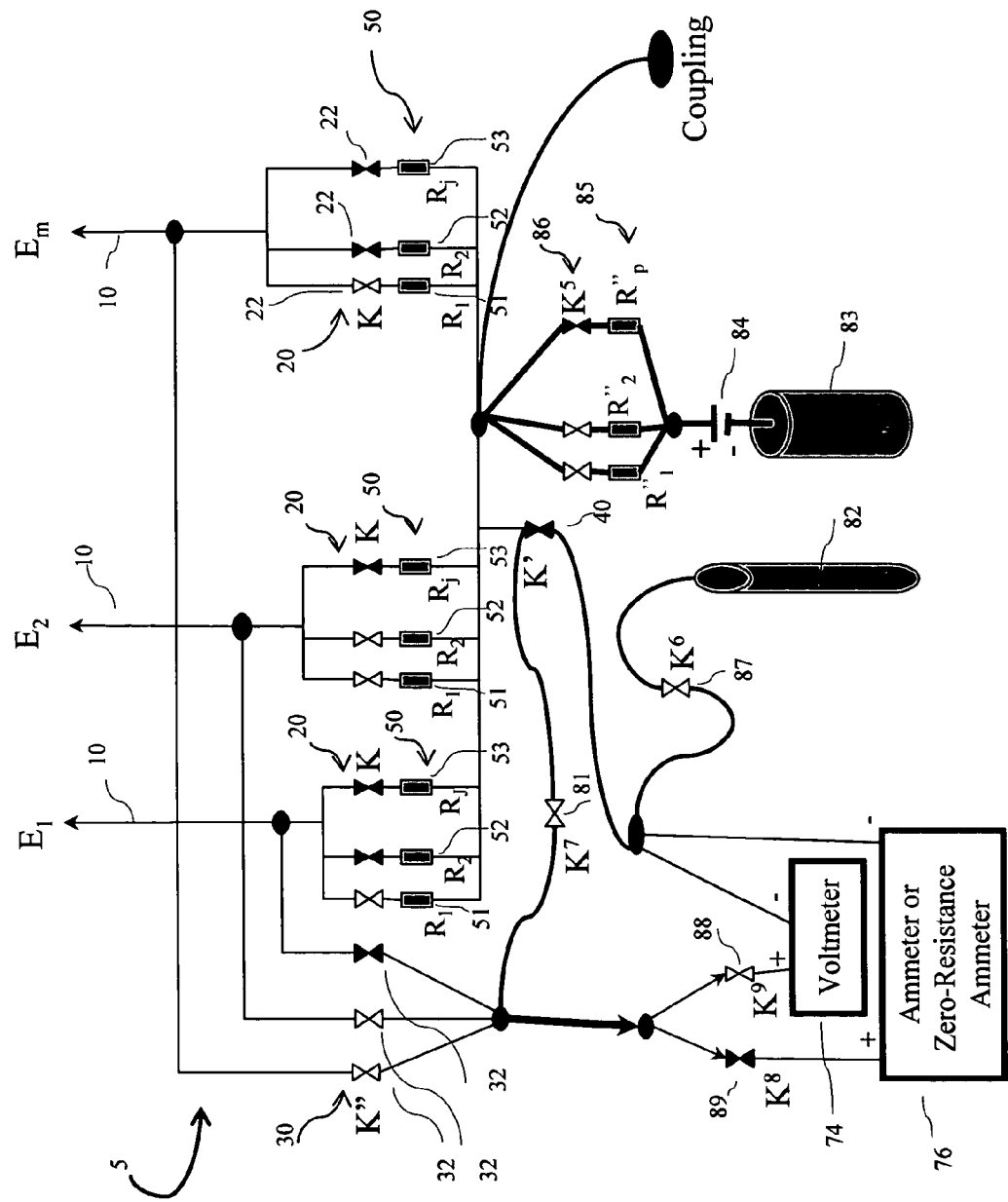
FIG. 6 is a schematic diagram showing the connection of the coupling joint of a multielectrode device to a cathode through a resistor element and a power source, and an ammeter for the measurement of the currents.

FIGS. 5 and 6 show how the setups shown in FIGS. 3 and 4 are used with an ammeter or a zero-resistance ammeter 76 to measure the coupling current from each electrode, respectively. A separate voltmeter 74 is required to measure the potentials of the electrodes connected to the electrode wires 10 and the potential of the coupling joint 12, so that the potential of the coupling joint can be polarized slightly above the highest open circuit potential measured from the individual electrodes. When the potential is measured, the $K^8$ switch 89 must be open and the $K^9$ switch 88 must be closed. The open-close states of the other switches are the same as those described in the description section for FIG. 3, for potential measurements.

Figure 7:
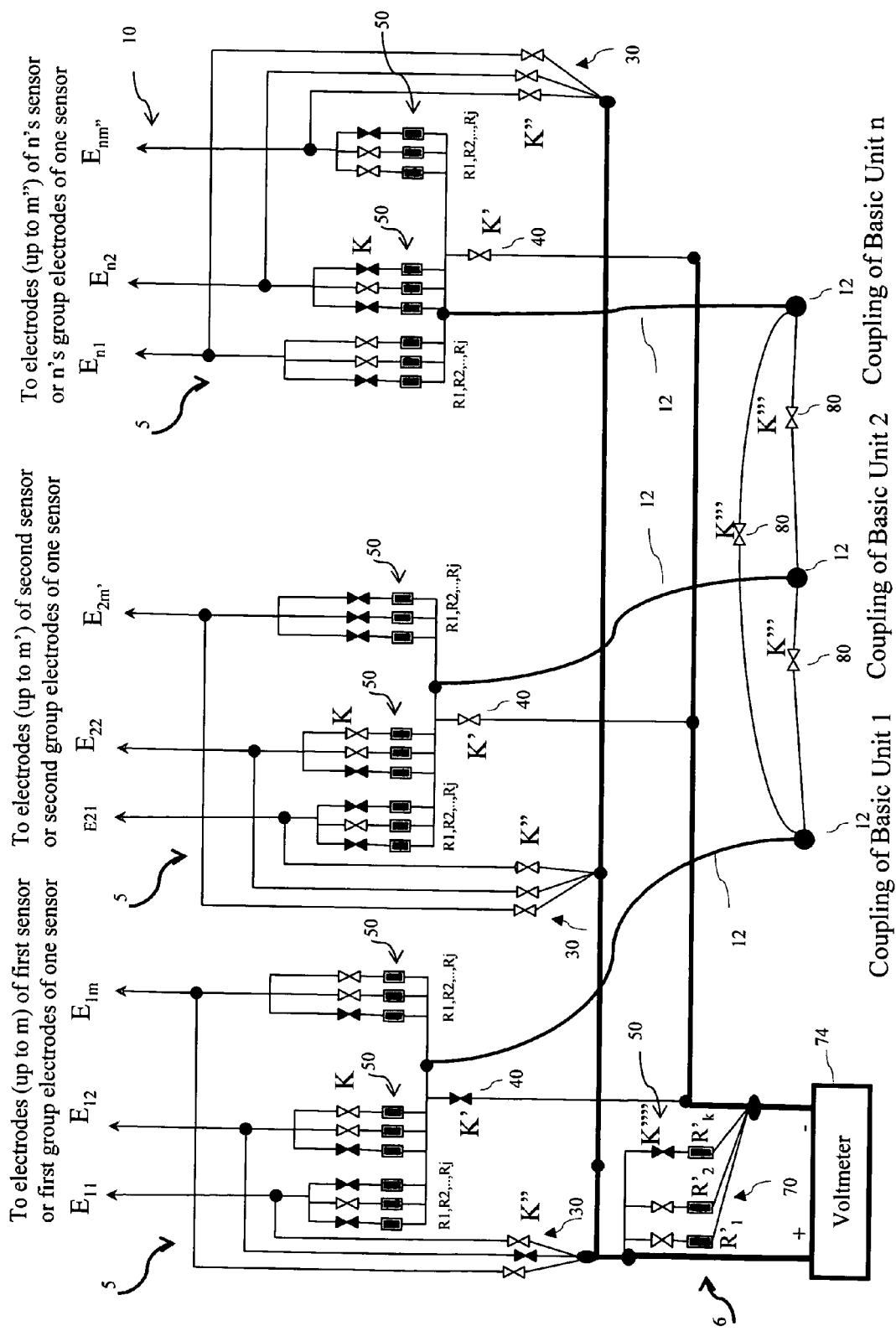
FIG. 7 is a schematic diagram of an integrated electronic system consisting of two or more basic electronic units for using a voltmeter to measure the coupling current from each electrode.

FIG. 7 shows a schematic diagram of an integrated electronic system. In this system, a voltage-measuring unit 6 that contains a voltmeter 74 is used to measure the coupling currents from a group of basic electronic units 5. Each of the basic electronic units is used independently for all the electrodes in one multielectrode device or for a group of electrodes in a multielectrode device or sensor. The grouping of the electrodes allows users the flexibility of using one instrument (or integrated electronic system) either for several devices or sensors (up to n, as shown in FIG. 7), or for one device or sensor that has more electrodes (up to the sum of the number of electrodes in each group). Each basic electronic unit may be considered as an independent group of channels of the integrated electronic system. The reader will have a better understanding of this flexibility after reading the description section for software (below). When any of the two or more basic electronic units 5 are used for one sensor and their coupling joints 12 need to be coupled, the corresponding K''' switches 80 (which can also be manual switches and controlled manually) should be closed. As in each single basic electronic unit discussed for FIG. 1, same or different values of resistors 50 or different combinations of resistors 50 may be used for the groups of basic electronic units 5 that are coupled together or used for one multielectrode device or sensor. The other features described for FIGS. 1 through 6, such as connections to a large electrode 14 through resistors 85, are not shown in FIG. 2, but can be easily understood by combining FIG. 7 with FIGS. 1 through 6.

Figure 8:
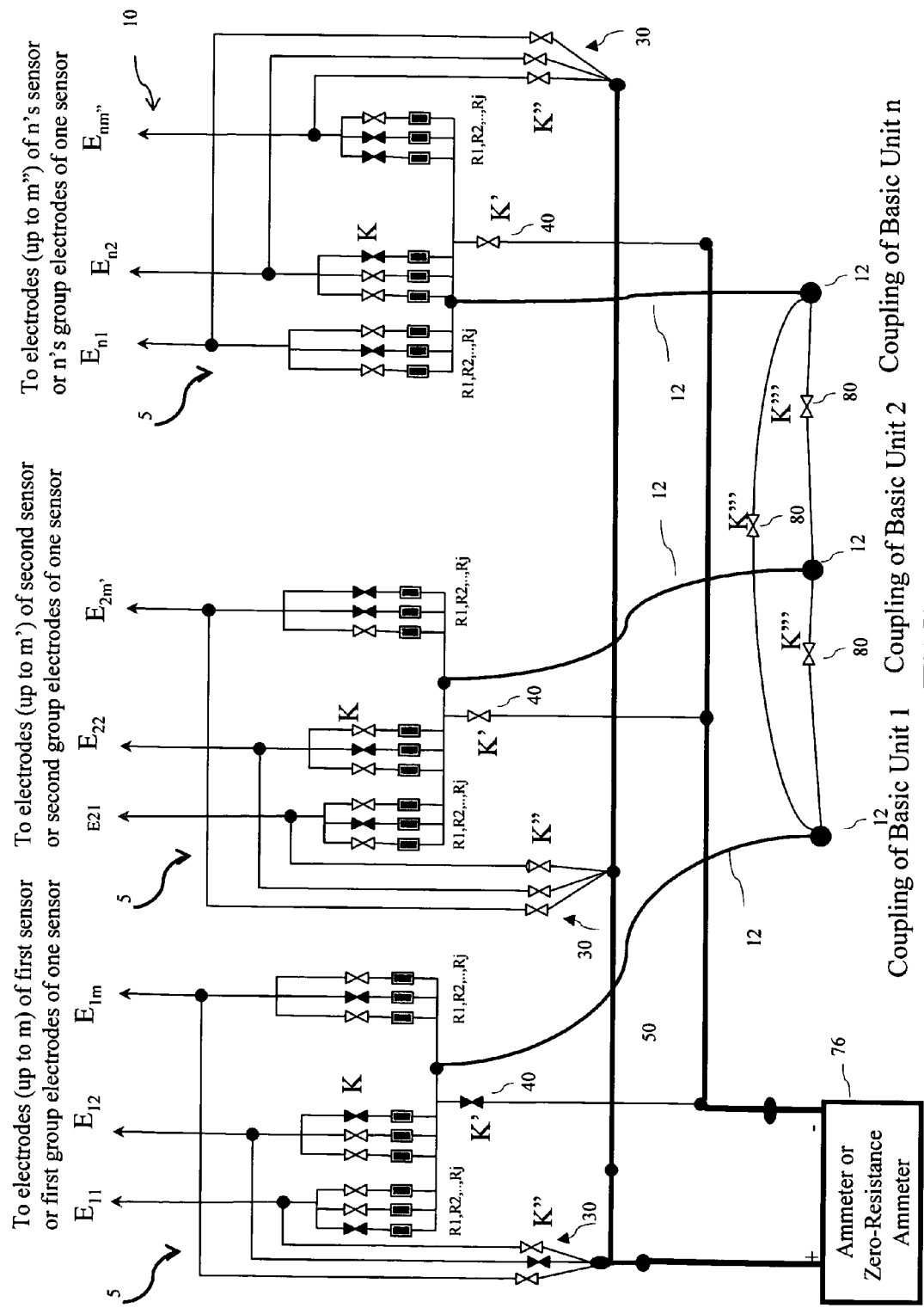
FIG. 8 is a schematic diagram of an integrated electronic system consisting of two or more basic electronic units for using an ammeter or zero-resistance ammeter to measure the coupling current from each electrode.

Similarly to FIG. 7, FIG. 8 shows the schematic diagram for using a zero-resistance ammeter or a regular ammeter 76, respectively, to measure the coupling current from the different electrodes connected to the electrode wires 10 of the n basic electronic units 5. The other features described for FIGS. 1 through 6, such as the measurements of the open-circuit potentials and the coupling potentials, are not shown in FIG. 8, but can be easily understood by combining FIG. 8 with FIGS. 1 through 6.

Figure 9:
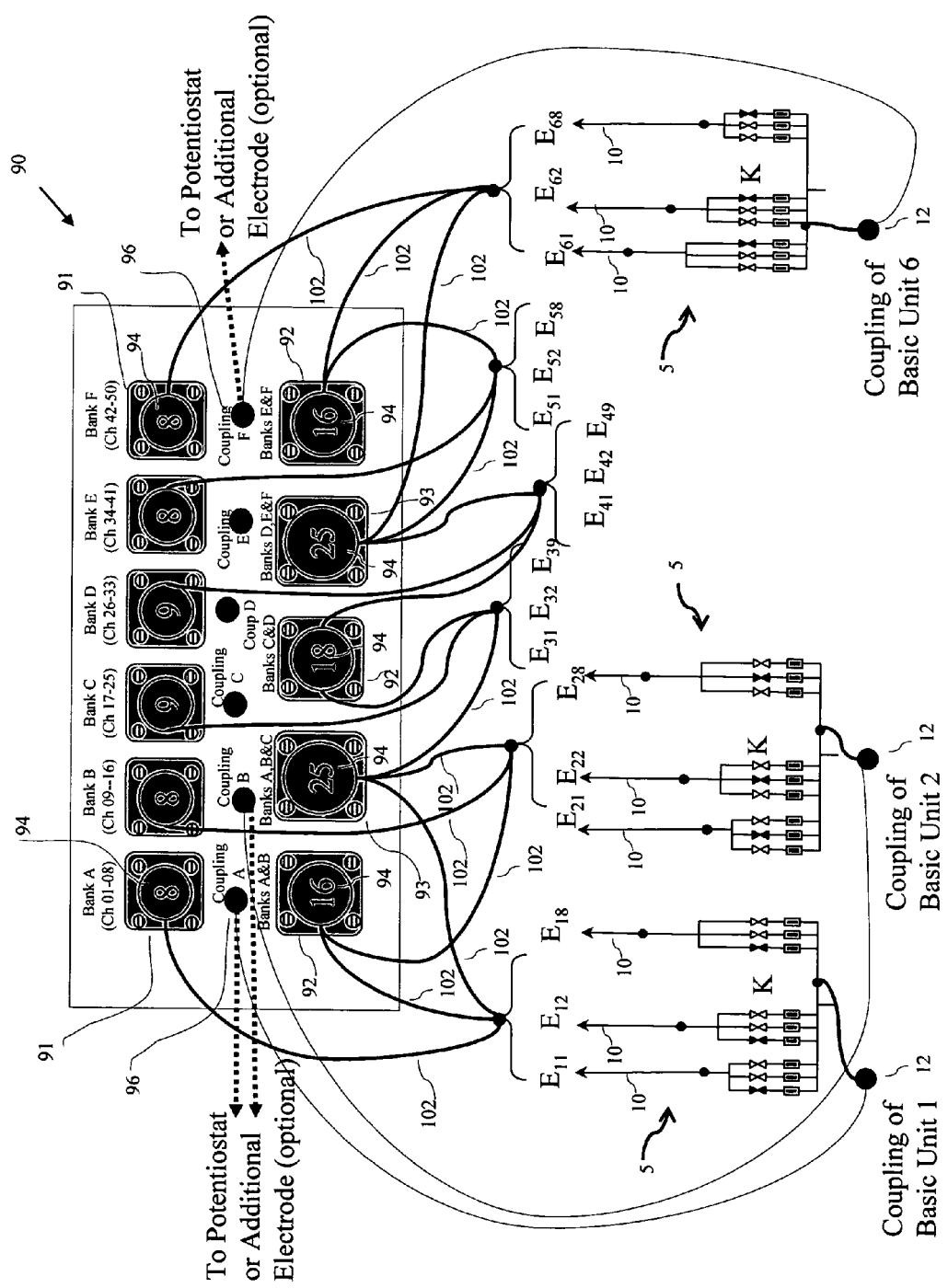
FIG. 9 is a schematic diagram for the connections from the electrode wires in the different basic electronic units to the connectors on a typical 50-channel instrument panel.

FIG. 9 shows an example of the connections between the electrode wires 10 of a group of the basic electronic unit 5 (FIGS. 7 and 8) and the electrical multi-pin connectors 91, 92, 93 on the instrument panel 90 through independent cables 102. The electrical connectors 91 for basic electronic units are designated as Banks A, B, C, . . . and F connectors, and they are connected to the $1^{st}$, $2^{nd}$, $3^{rd}$, . . . and $6^{th}$ basic electronic units, respectively. The electrical connectors 92 for two combined basic electronic units are designated as Banks A&B, C&D, and E&F connectors, and they are connected to the $1^{st}$ and $2^{nd}$, $3^{rd}$ and $4^{th}$, and $5^{th}$ and $6^{th}$ basic electronic units, respectively. The electrical connector 93 for three combined basic electronic units are designated as Banks A, B&C, and Banks D, E&F connectors and they are connected to the first three ($1^{st}$, $2^{nd}$, and $3^{rd}$) and the last three ($4^{th}$, $5^{th}$ and $6^{th}$) basic electronic units, respectively. Although not shown in FIG. 9, there may be other connectors in the panel. For example, a connector with an even larger number of pins may be used to connect all of the six combined basic electronic units.

Therefore, a user can use this instrument for: six sensors on electrical connectors 91, each having up to 8 or 9 electrodes, as indicated by the numerical number 94 in FIG. 9; three sensors on electrical connectors 92, each having up to 16 or 18 electrodes, as indicated by the numerical number 94 in FIG. 9, or two sensors on electrical connectors 93, each having up to 25 electrodes. A 50-pin electrical connector may also be added to the panel and connected to all of the six basic electronic units and used for a sensor having up to 50 electrodes. The users may also have other options. For example, they can use one 25-electrode sensor (with Banks A, B&C connector) and two 8-electrode sensors (with Banks E and F connectors) and one 9-pin electrode sensor (with Bank D connector).

When a connector is connected to more than one basic electronic unit, the coupling joints of the corresponding basic units are usually connected by switching on the corresponding K''' switches 80 (see FIGS. 7 and 8). For example, if Banks A, B&C connector is connected to a sensor, the coupling joints 12 of the $1^{st}$, $2^{nd}$, and $3^{rd}$ basic electronic units 5 should be connected together. However, the user has the option of not switching on the corresponding K''' switches 80 when using a connector connected to more than one basic electronic unit for one sensor. For example, if a sensor with 25 electrodes is connected to Banks A, B&C connector, the user may choose not to connect the coupling joints 12 of the $1^{st}$, $2^{nd}$, and $3^{rd}$ basic units 5. In this case, the user divides the electrodes in the sensor into three groups and the one 25-electrode sensor works as three sensors (two are 8-electrode sensors and one is a 9-electrode sensor). By properly specifying the options through use of the software (see the software section), the user may have three processed sensor signals, such as: three corrosion rates, three corrosion potentials, and three penetrations. By doing so, the user may check the reproducibility of three sub-sensors on a large sensor. However, it should be cautioned that the signals from an 8-electrode sensor may not be as reliable as the signals from a 25-electrode sensor according to the statistic principles.

FIGS. 10 Through 17—Software

Figure 10:
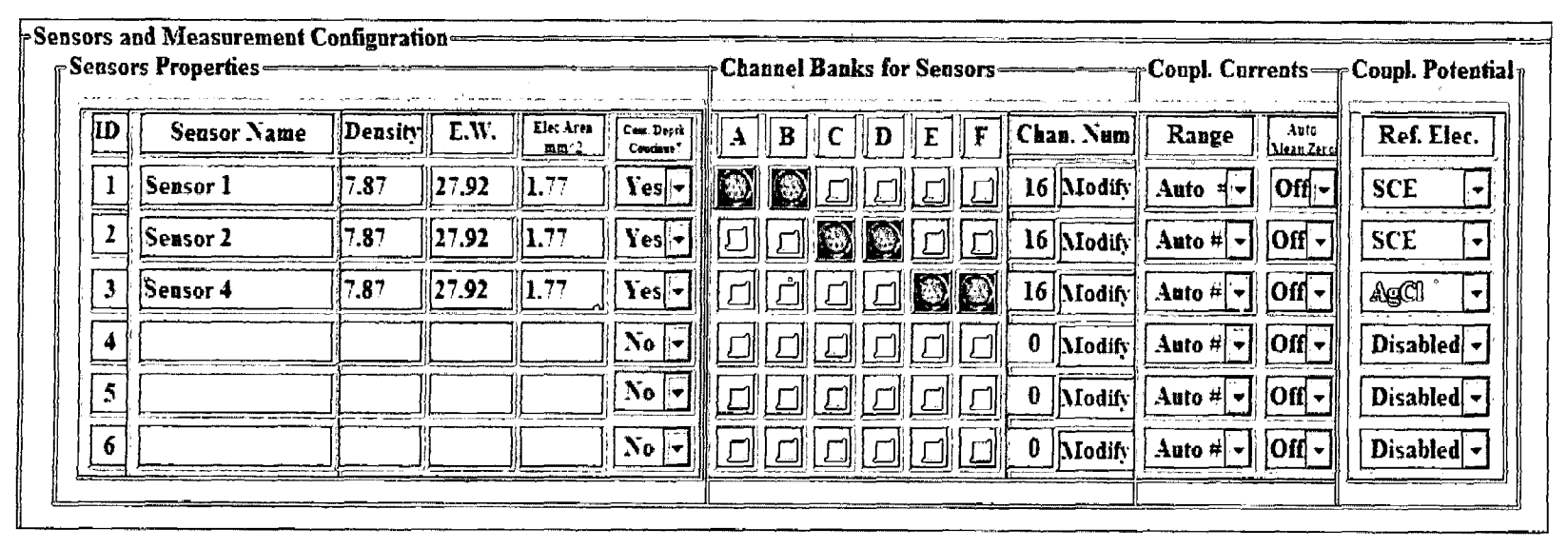

FIG. 10 shows one of the software interfaces for setting up the connections between the multielectrode devices or sensors and the connector banks 91, 92, and 93 on the instrument panel 90. In FIG. 10, Sensors 1, 2, 4, and 6 use connector Banks A through D, respectively; Sensor 7 uses Bank F; and Sensor 9 uses Bank E. The Chan. Num. (channel number, or called the active pin number or electrode number) is the number of active channels or active pins on a connector (Note: the numerical number 94 in FIG. 10 is the number of pins available for measurement on a connector). The Chan. Num. can be modified, by clicking the corresponding Modify button (see below for details). The Density, E. W (Equivalent Weight) and Elec. Area (electrode surface area in $mm^2$) parameters are required by the software, to calculate the corrosion rate, in terms of depth per unit time (or growth rate, if the instrument is used to study the electroplating processes) and corrosion penetration, in terms of depth. The Auto Mean Zero option is used to tell the software whether or not to automatically correct the bias currents according to the multielectrode sensor principles. As discussed earlier (see the discussion section for FIG. 1), when the coupling joint is not connected to a separate electrode, the sum of the cathodic and anodic currents from a coupled multielectrode device or sensor should be zero and the mean value should also be zero. Any deviation from zero is caused by an error or bias current and should be corrected. The Reference Electrode option specifies which reference electrode is used to measure the potential of a multielectrode device or sensor (the potential at the coupling joint 12), using the voltmeter 74 in the measuring unit 6, as shown in FIGS. 3 through 6.

The Range option specifies which range of the instrument to use; usually the Auto range is used. The number of ranges on the basic electronic unit equals the product of j and k (or j times k), as shown in FIG. 1.

The Cum. Depth Continue? option is used to specify whether a user wants to continue the penetration depth calculation based on the depth already corroded in a previous experiment. If "No" is selected, the depth calculation will be started fresh, which simulates the case that the sensor electrodes were polished or re-polished prior to the start of the measurement. Very often, the user needs to temporarily stop the running of the software program to make some changes to the experiment or the software may be stopped by unexpected events, such as power failures. In these cases, the user can continue the real-time depth calculation after restarting the software, by clicking the "Yes" button. The software program saves the depth information (or cumulative charge) in a data file for each electrode on each sensor every time a new cycle of data is available. When the program is restarted, these data will be loaded from the data file, if the "Yes" to continue button is selected and used to continue the depth calculation.

Figure 11:
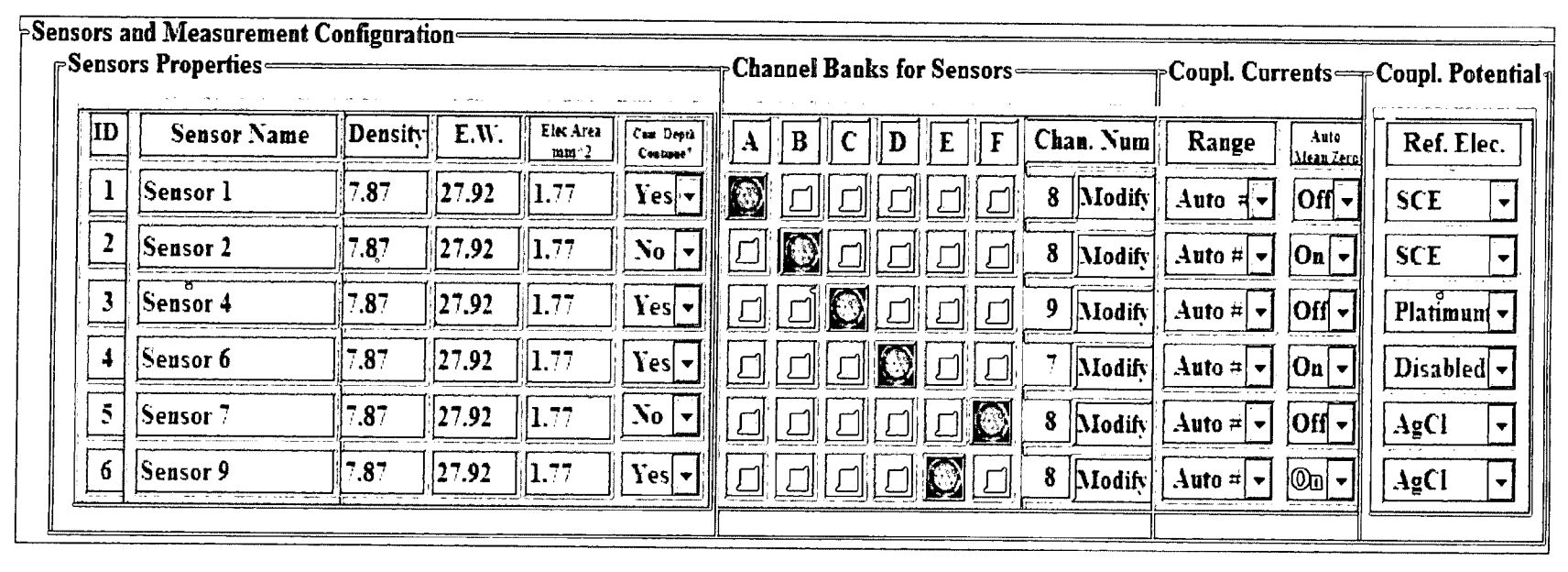

FIG. 11 shows a variation of the specifications for the software interface, as shown in FIG. 10. Here, Sensor 1, which has 16 active electrodes, uses Banks A and B; Sensor 2, which has 16 active electrodes, uses Banks C and D; and Sensor 4, which also has 16 active electrodes, uses Banks E and F. In FIG. 11, a user can utilize any combination of the connectors 91, 92, and 93 for a given sensor. For example, the user can use Banks A, B, D, E and F connectors for a sensor. If the sensor only needs a portion of the pins on some of the connectors, the user needs to go to FIG. 12 to deactivate those that are not required (see next paragraph).

Figure 12:
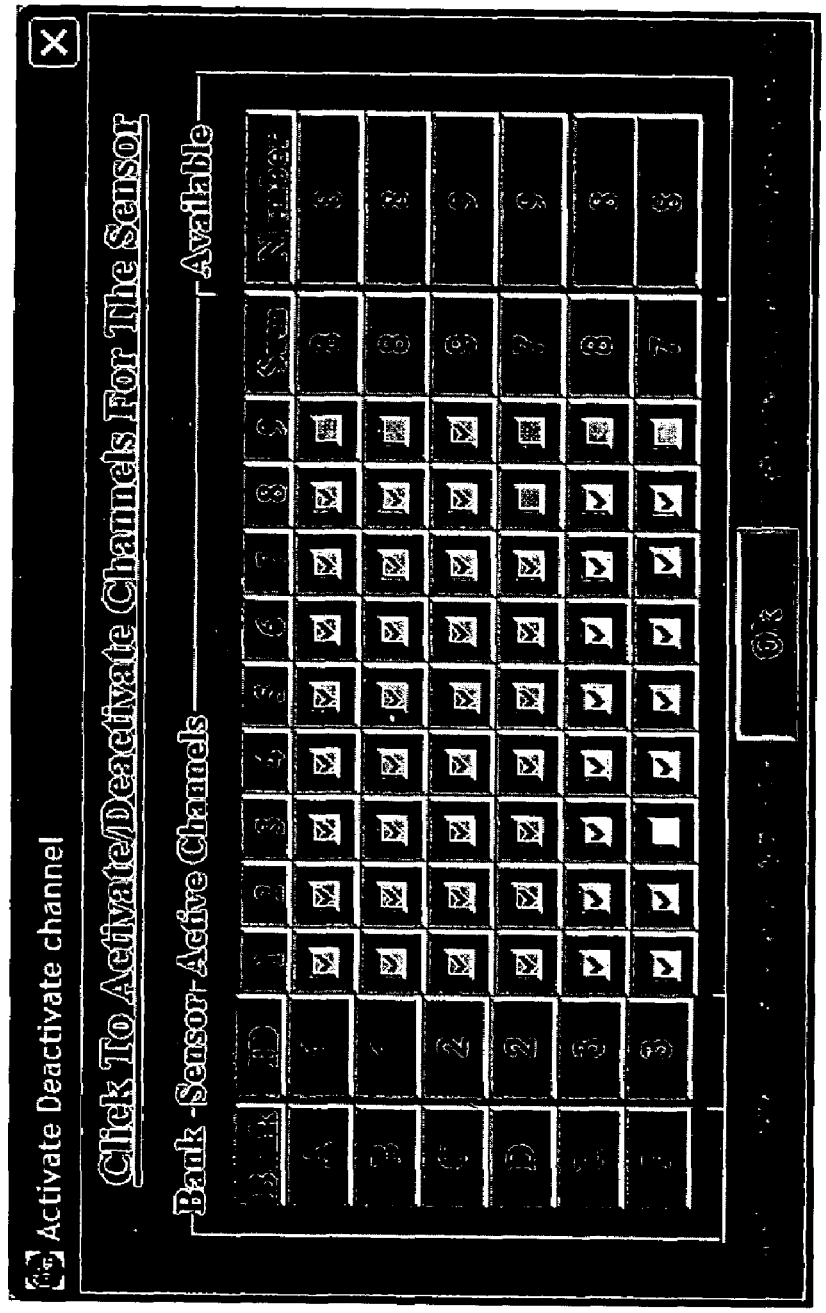
FIG. 12 shows a software interface for specifying which pin/channel is active and which pin/channel is inactive for each bank of connectors.

FIG. 12 shows the software interface for specifying which pin/channel (or electrode wire 10) is active or inactive for each bank of connectors 91, 92, and 93. The user can click on a check box in FIG. 12 to activate or deactivate the corresponding pin/channel. The number in the Sum column is automatically calculated after the user activates or deactivates a pin/channel. The numbers in the Available Number column are the values of m, m', and m", as shown in FIGS. 7 and 8, or the numerical number 94, as shown in FIG. 10, and they are fixed at the instrument design time. In FIG. 12, Pin 3, on Connector Bank F, and Pins 8 and 9, on Connector Bank D, are deactivated. These three pins are available on the instrument, by design.

Figure 13:
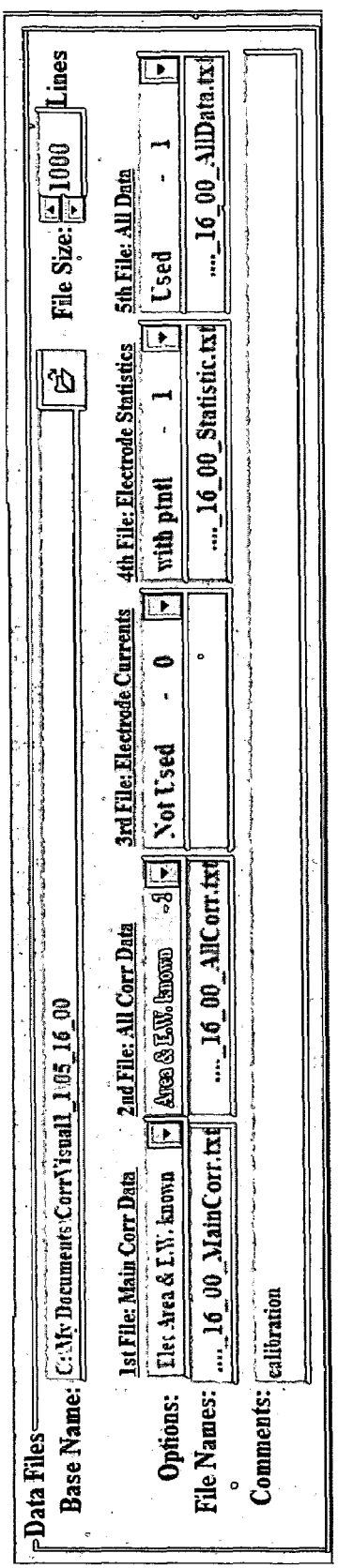
FIG. 13 shows a software interface for specifying the data files to save during the measurements.

FIG. 13 shows the software interface for specifying which data files will save the collected and the processed data during the measurements. Because of the large number of data available from multielectrode devices or sensors, the data are saved into five files according to their category or type. The first file contains the main corrosion data, such as the corrosion rate, the penetration depth (if the sensor electrode area and E.W. are given), the corrosion potential for each sensor, and the temperature. The corrosion current and corrosion cumulative charge will be saved, instead of the corrosion rate and penetration, if the electrode area and the E.W. are not given. The second file contains all corrosion-related data, such as corrosion current, corrosion current density, corrosion charge, corrosion charge density, corrosion rate, corrosion depth, corrosion potential, which electrode is corroding the most, and which electrode has corroded the most on each sensor at each time interval. The third file contains the currents from all electrodes, on every sensor. The user has the option to not save the corrosion potential to reduce the file size. The fourth file contains the statistics for the signals from all electrodes in each sensor. The statistical parameters include the mean, minimum, maximum and standard deviation of currents, and minimum and maximum charges for each sensor. The user also has the option to choose not to save the corrosion potential data for each sensor to reduce the file size. The fifth file contains all available data. The other options are self-explanatory. A user always has the option to eliminate use of any of the files, in order not reduce total memory. This kind of file saving method provides great flexibility in using the instrument. For example, a plant operator is usually concerned with only the corrosion rate. Therefore, he or she can choose to disable all the other files. On the other hand, a researcher in an electrochemical laboratory may want to gather and keep all the information from a multielectrode device or sensor. In this case, he or she may want to enable only the fifth file or only the first four files.

Figure 14:
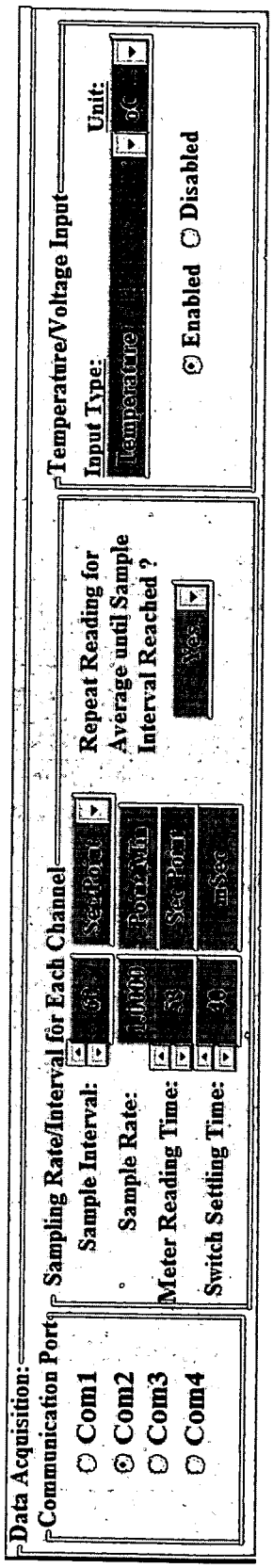
FIG. 14 shows a software interface for specifying Meter Reading Time, Switch Settling Time and if readings are to be repeated during one Sample Interval.

FIG. 14 shows the software interface for specifying Meter Reading Time (for the voltmeter 74 plus the electronic unit 5 or integrated electronic system), Switch Settling Time, and whether a user wants to Repeat Readings for Averaging during a given time interval. The Sample Interval is the time interval a user specifies to sample one data point for every active electrode connected to the instrument. The Meter Reading Time indicates the time it takes for the meter to read once from all the electrodes. The Switch Settling Time indicates how long a user wants the meter to wait after the K" switch (see FIG. 1) is switched on before taking the reading for an electrode. The user can adjust this time to minimize the effects of the spikes that may be produced by the switching. If the settling time is long enough, the meter will start to take readings after the spike has disappeared. The Meter Reading Time includes the Switch Settling Time and the integration time for taking the reading for every channel (or electrode). If the Meter Reading Time is set long enough, the meter will take the maximum possible integration time to get a stable and accurate reading before going to the next channel (or electrode). In many cases, the Meter Reading Time is much shorter then the Sample Interval. Therefore, the meter is able to repeat the reading cycle many times and then get an averaged result for each electrode at the end of the Sample Interval to filter out possible noise effect. Users can do so by selecting the option of "Repeat Reading for Averaging until the Sample Interval Reached." This filtering is important for the measurement of extremely low corrosion rates (down to 10 nm/year) or low currents (down to 10 pA). The other features in this interface are self-explanatory.

Longer Meter Reading Time means longer integration time or better filtering for taking one reading from each electrode. More repetition in one Sample Interval also means better filtering for taking one reading from each electrode. However, the difference is that the longer Meter Reading Time also means that the time interval between taking the reading from the first active electrode and taking the reading from the last active electrode is longer. In some cases, this longer time interval is not tolerated because the readings from the different electrodes should be taken at nearly the same time. In this case, filtering based on repetition (or averaging) of the readings from many cycles may be a better option than the long Meter Reading Time, because each cycle of readings for all of the active electrodes are collected in a relatively short period of time (within one Meter Reading Time).

Figure 15:
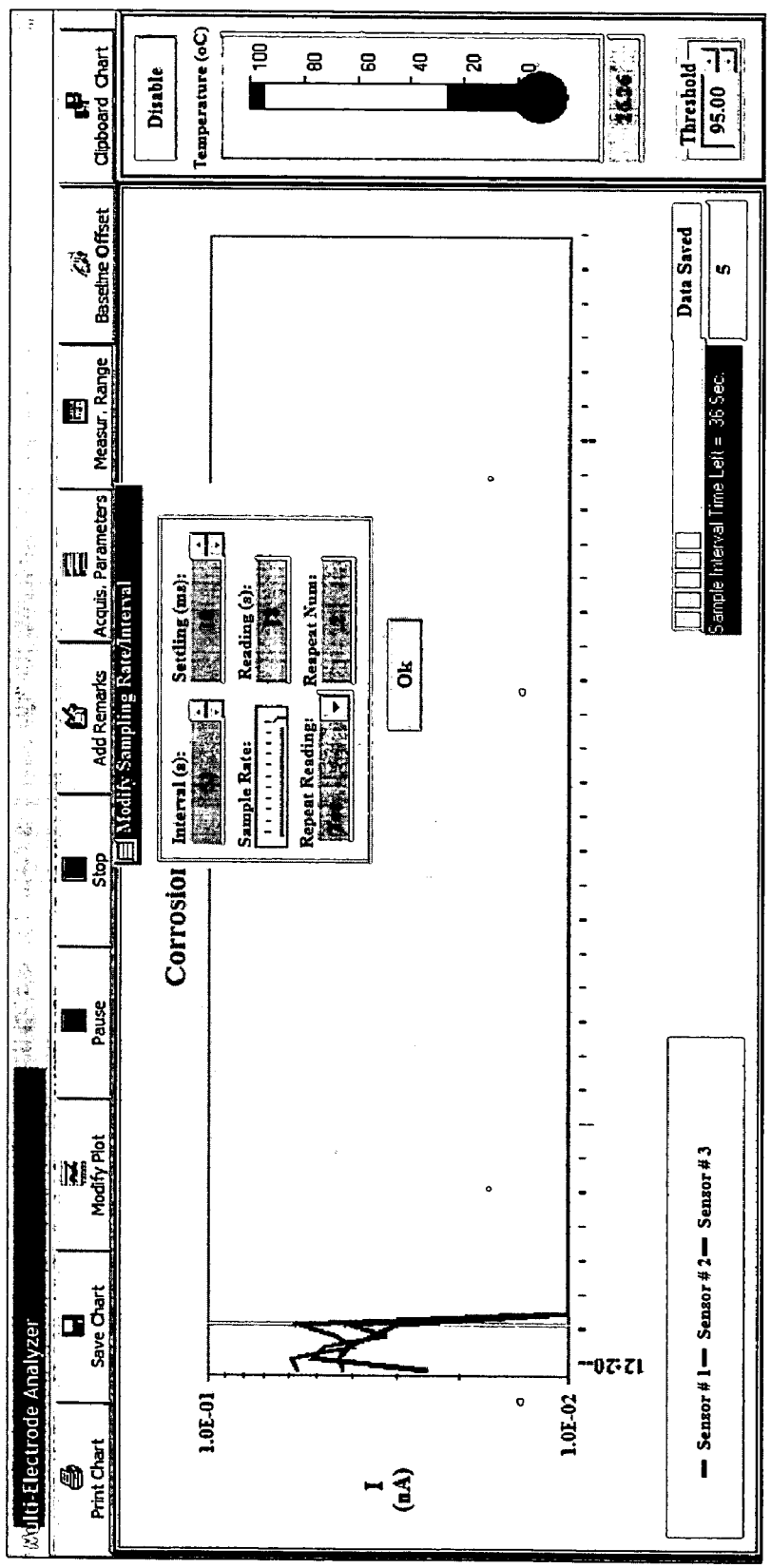
FIG. 15 shows a software interface for the measurement.

FIG. 15 shows the software interface that appears during measurement or monitoring. This interface not only dynamically displays the measured data, but also allows a user to change the data acquisition parameters, such as the Sample Interval, Settling Time, and Sample Rate, during the measurement. The interface also allows a user to pause the measurement, in order to alter the experiment (i.e., taking a sensor out of a monitoring location to inspect the degree of corrosion taking place on the electrode surfaces). The measurement range for each sensor can also be changed from this user interface.

The Add Remarks option is like an electronic notebook. This button allows a user to add remarks; the software will automatically record them and the time they are made into the Remarks column of every data file and into a separate Remarks file. The software also automatically records all the changes the user made to the program, such as Measure Range changes (including the old range and the new range) or Acquis. Parameters changes (including the parameter name, and the old value and the new value) to the Remark column of every data file and to the separate Remarks file.

Figure 16:
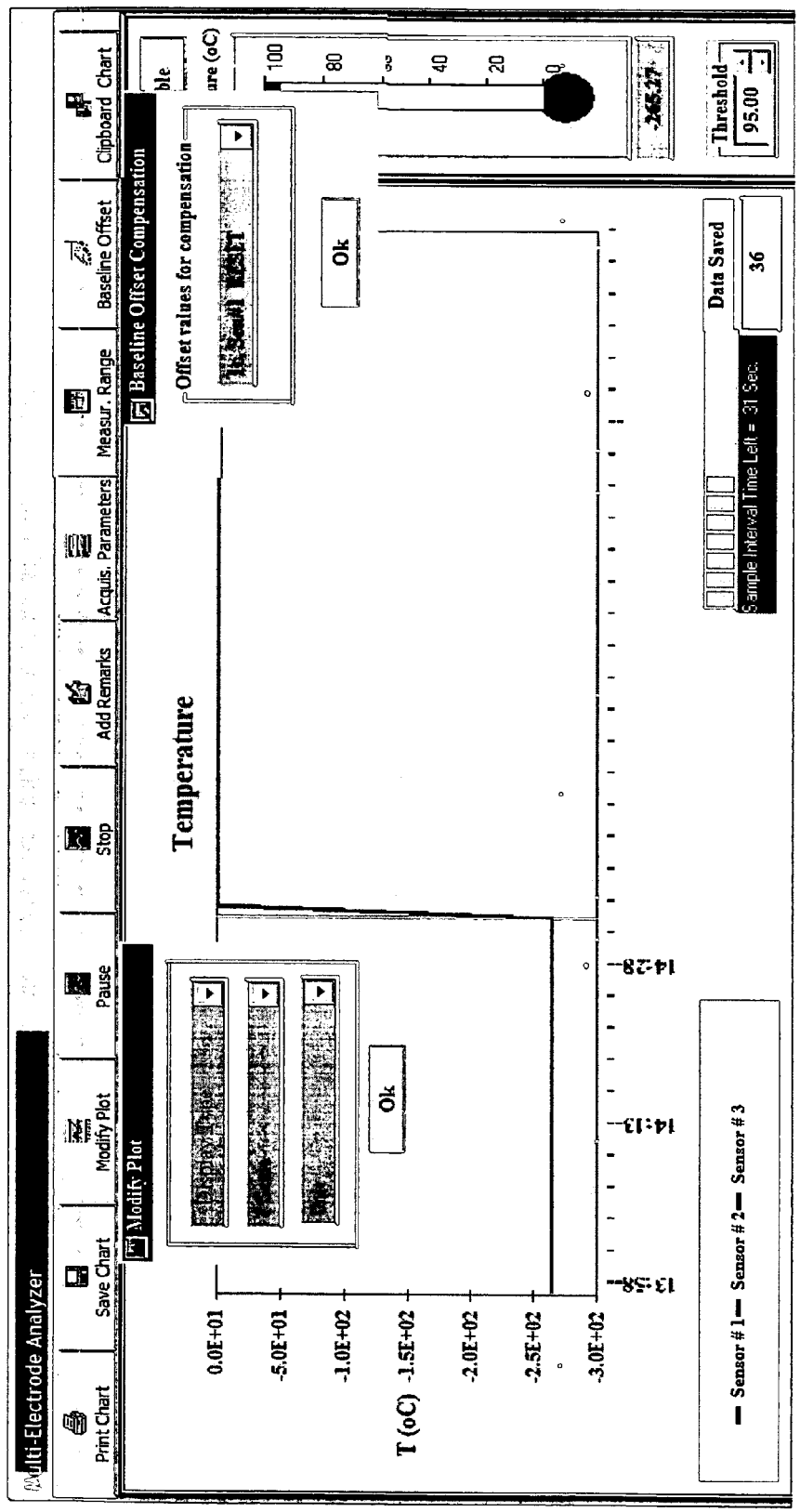
FIG. 16 shows a software interface for measurement with the features of Modify Plot and Baseline Offset corrections.

FIG. 16 shows the features of Modify Plot and Baseline Offset corrections on the software measurement interface. The Baseline Offset button allows a user to reset, disable/enable or obtain new baseline offset values. The baseline offset for each channel is the current measured when that channel is connected to a zero current source. Because the instrument measures currents by measuring the voltages across the resistors or by using an ammeter (see FIGS. 1 through and 6), such low levels of baseline offset are usually caused by the thermoelectric effect from the electrical contacts. The baseline offset values for each channel (or electrode) can be measured while the sensor is placed in dry air, where it should have zero corrosion currents and be stored in the memory of a controller or a computer. These offset values, if the option on the interface is enabled, are used by the software to automatically correct the small baseline offset errors from each electrode for better accuracy. The software is also able to display different types of dynamic plots (including the corrosion rate, corrosion penetration depth, corrosion current, corrosion current density, corrosion potential, and temperature).

FIG. 17 shows that the software measurement interface dynamically displays the numerical values for the currents from all electrodes and the statistic parameters, such as minimum, maximum and mean, and the corrosion rate and corrosion potential for each sensor.

Figure 18B:
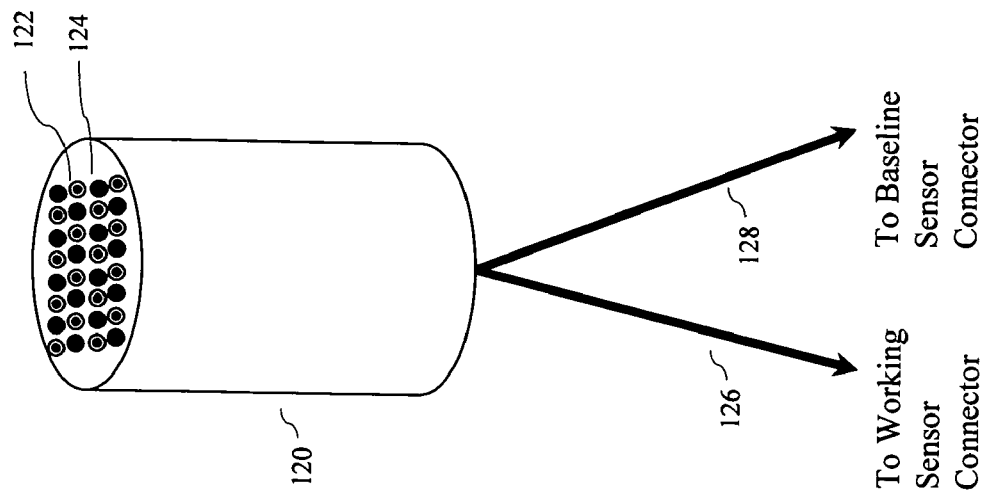
FIG. 18B is a schematic diagram for a dual-sensor system to reduce the effect of the non-corrosion related anodic reactions on the sensor signals for a Combination Sensor Design.
Figure 18A:
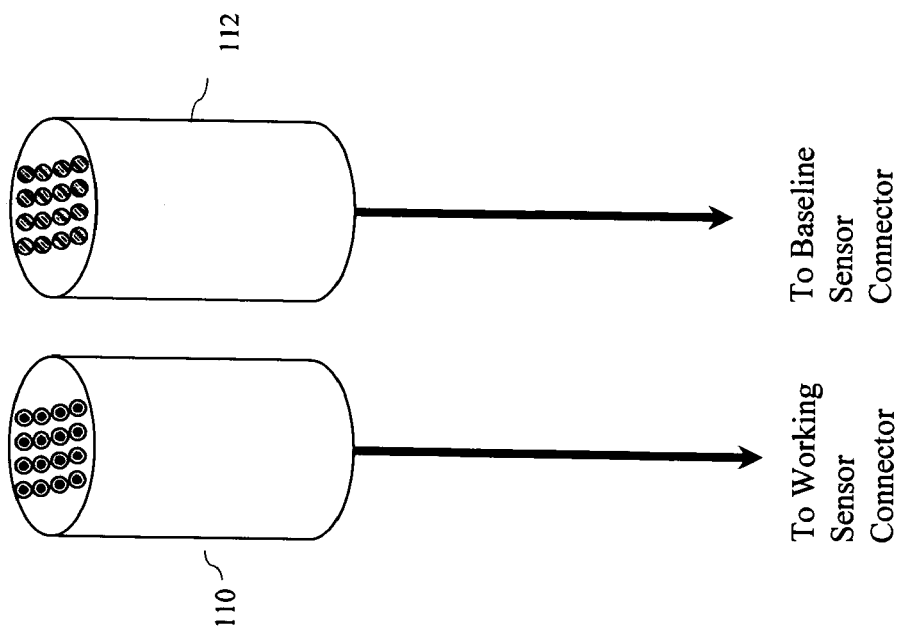
FIG. 18A is a schematic diagram for a dual-sensor system to reduce the effect of the non-corrosion related anodic reactions on the sensor signals for a Dual-Sensor Design.
Figure 19:
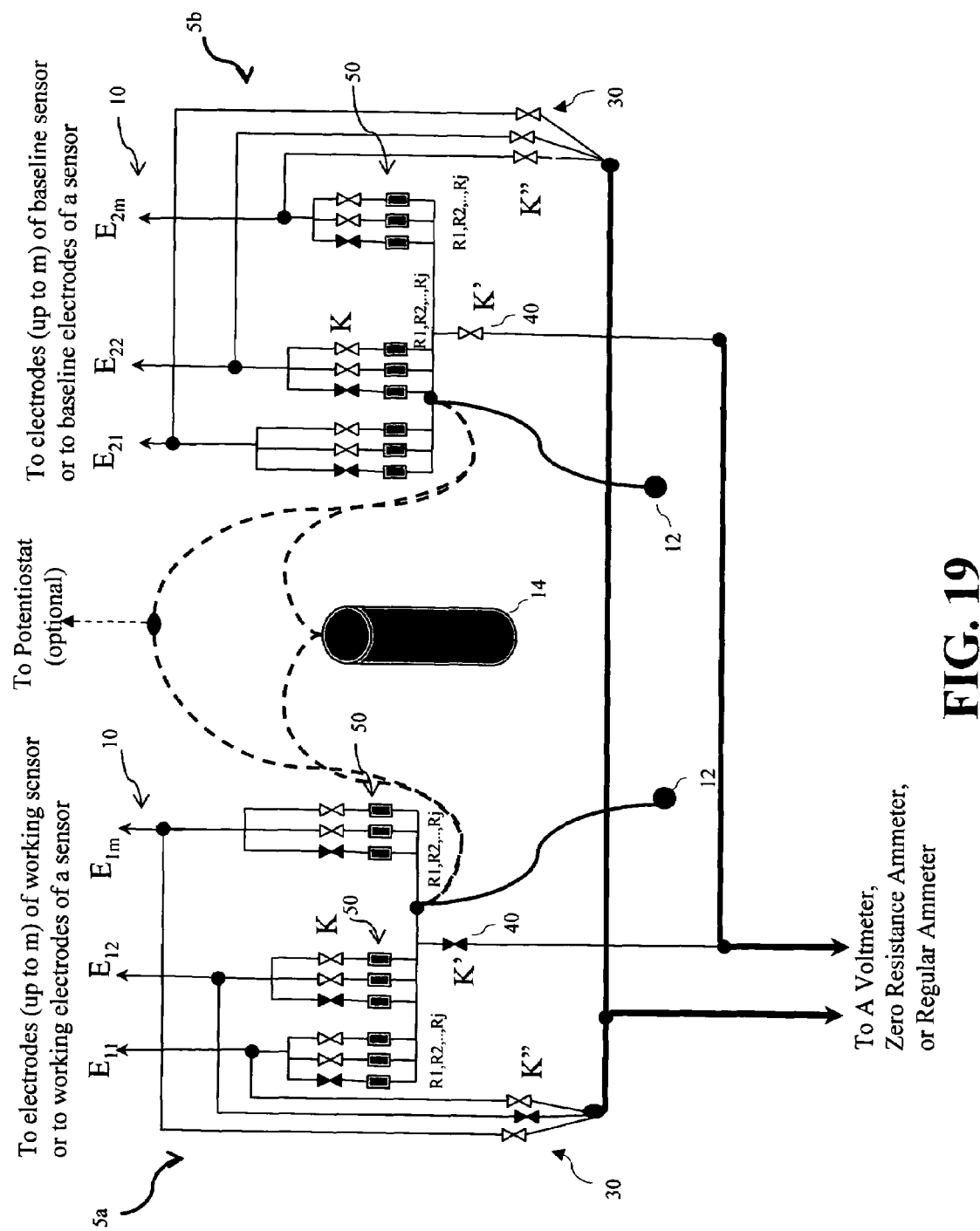
FIG. 19 is a schematic diagram of a differential electronic circuit for the dual-sensor multielectrode sensor system used in environments containing electrochemically active agents.

FIGS. 18 and 19—Dual-Sensor Coupled Multielectrode System for Corrosion Monitoring in Environments Containing Electrochemically Active Agents and for Biofilm Activity Monitoring When the coupled multielectrode sensors are used as corrosion sensors, an important assumption is that all the anodic electrochemical reactions taking place at the anodic electrodes are assumed to be due to the corrosion reaction (dissolution) of metals. In reality, this may not be true in an environment that contains a significant amount of reducing agents. In such a system, a dual-sensor system may be used. The dual-sensor system comprises essentially two sensors. The first one is the working sensor that is a regular coupled multielectrode sensor made of the sensing material whose corrosion rate is to be monitored. The second sensor is a baseline sensor made of the sensing material that does not corrode, but allows the oxidation of the reducing agents to take place on its surface in a way that is similar to that on the sensor electrode surfaces. The difference between the signal from the working sensor electrodes and the signal from the baseline sensor electrodes may be used as the corrosion signal.

A dual-sensor system may be of a dual-sensor design (FIG. 18a) or a combination-sensor design (FIG. 18b). The dual-sensor design has a working sensor 110 and a baseline 112 sensor. In the combination sensor 120, the working sensor electrodes 122 and the baseline sensor electrodes 124 are placed close to each other and are exposed to the same environment and fluid flow pattern. Separate cables, 126 and 128, are used to connect the working sensor electrodes 122 and the baseline sensor electrodes 124 to an integrated electronic system as show in FIG. 19 (below). The combination sensor design may be a better choice for most applications. However, the dual-sensor design may be used where the sensor size cannot be too large. The dual-sensor design also allows the user to frequently make maintenance such as polishing to the working sensor 110 without the need to do anything to the baseline sensor 112. The other advantage of separating the two types of sensor electrodes is that a single baseline sensor 112 can be used for many working sensors 110.

In practice, if the working sensor is made of carbon steel material, the baseline sensor may be constructed with stainless steel material. If the working sensor is made of stainless steel material, the baseline sensor may be constructed with Alloy 276. However, noble metals, such as platinum, should be avoided, because they may catalyze the oxidation reaction of the reducing agents differently from that of the working sensor electrodes.

FIG. 19 shows a schematic differential electronic circuit to use with the dual-sensor system shown in FIG. 18, which has essentially two basic electronic units: 5a for the working sensor and 5b for the baseline sensor. The software discussed in the previous section may be slightly modified to use with the dual-sensor system and the differential electronic circuit. In order for the baseline sensor electrode to effectively simulate the non-corrosion anodic reactions, its electrode potential should be controlled at the same potential as that of the sensor electrodes. A potentiostat or a large electrode 14 may be used for this purpose.

The baseline sensor shown in FIG. 18 (with or without the working sensor) may also be used, like the BioGeorge Sensor (see J. G. Licina, "Monitoring Biofilms on Metallic Surfaces in Real Time," Paper No. 442, Corrosion/2001, NACE International, 2001), to detect biofilm activities. If the baseline sensor produces significant signals in a bacteria-containing environment, but does not produce significant signals in a sterile environment (after the same solution going through a bio-filter, for example), then the signal produced in the bacteria-containing environment must be due to the biological activity. Such a bio-activity sensor may be used for in situ and real-time measurement of bio-activities.

Figure 20:
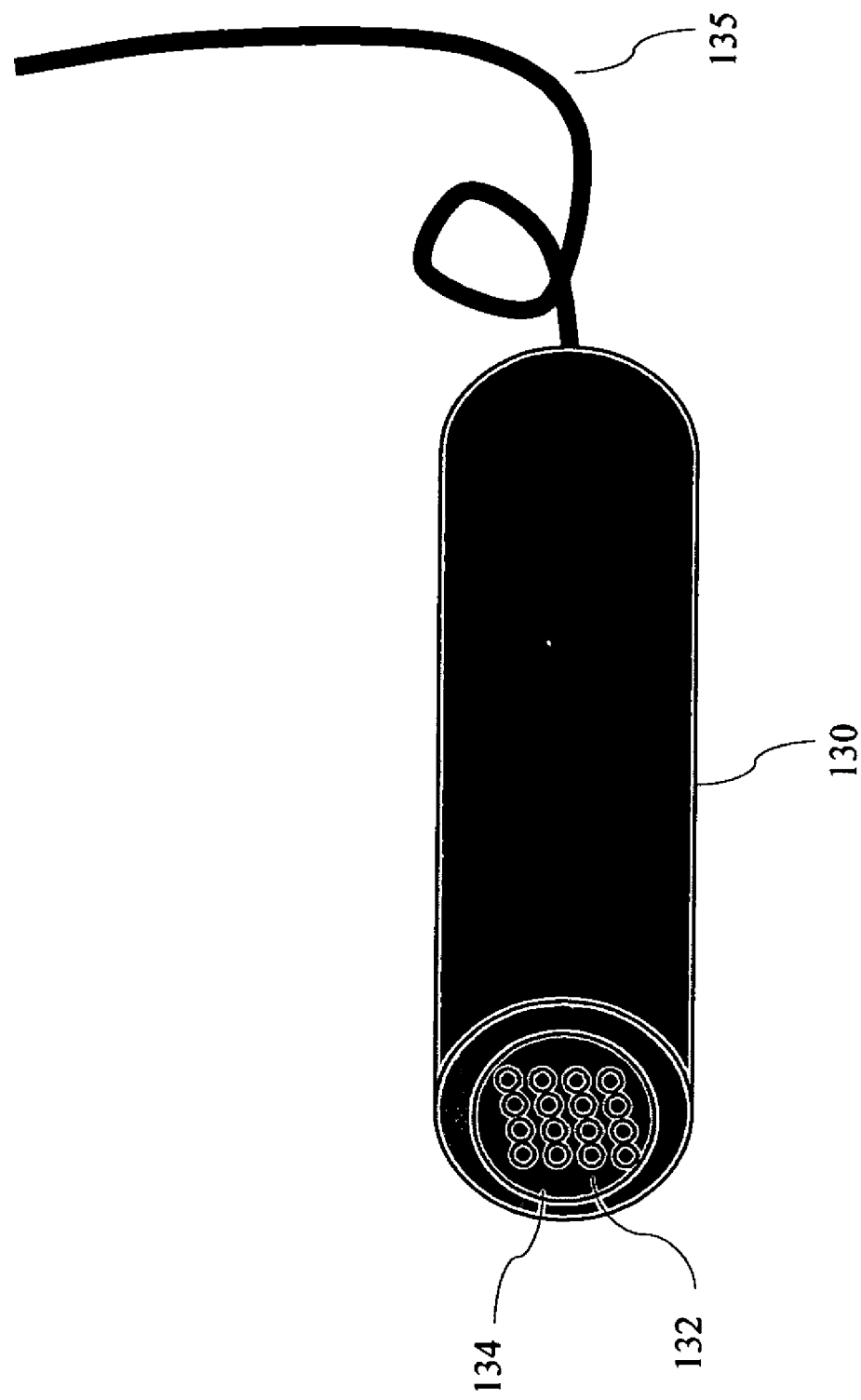
FIG. 20 is a schematic diagram for a typical multielectrode sensor.

FIG. 20—Selection of Sensor Body Material to Avoid Contamination of Sensing Electrodes by Body Material During Fabrication or Re-Surfacing and Method for Cleaning Contaminants It was noticed that if the corrosion resistance of the probe body or probe protection tune 130 (FIG. 20) is not better than that of the sensing electrode 132, the sensing electrodes 132 were very often contaminated by the probe body material during fabrication or during re-surfacing (polishing) and gave faulty signals during service. During the measurements, the software described earlier must decouple many of the malfunctioning electrodes. To avoid possible contamination of the electrode by the probe body material during fabrication or re-surfacing (polishing), the probe body 130 must be made with more corrosion-resistant materials than the probe sensing electrode 132, or made of non-corroding material (i.e., plastics). For example, if the probe electrode 132 is made of Type 316 stainless steel, the probe body 130 should be made of a material such as Alloy 276.

Even if the probe body 130 material is more corrosion resistant than the sensing electrode 132 material, the fine metal particles of both the probe body 130 and the sensing electrode 132 materials, which are generated during fabrication or re-surfacing of the probe, may get stuck on the sensing electrode 132, mostly between the electrodes 132 and the insulation 134 material (see FIG. 20). These metal particles may still give faulty signals, because they have high surface areas. Electrochemical cleaning in a dilute acid solution, or in the same monitoring solution in situ, may be used to remove these more reactive or fine particles.

A cyclic potential sweep method may be used to clean the electrode; especially to clean the contaminants attached to the sensing electrode surfaces in situ during service. Triangle- or square-voltage waveforms may be built in the basic electronic units 5, as shown in FIGS. 1 through 9, and applied by the software to the malfunctioning electrodes after they are identified as the malfunctioning electrodes, according to the statistical parameters. For example, if the current signal from a particular electrode is outside a certain range near the average value of the currents from all electrodes of a sensor based on statistical analysis, this electrode may be considered to be contaminated.

Figure 21:
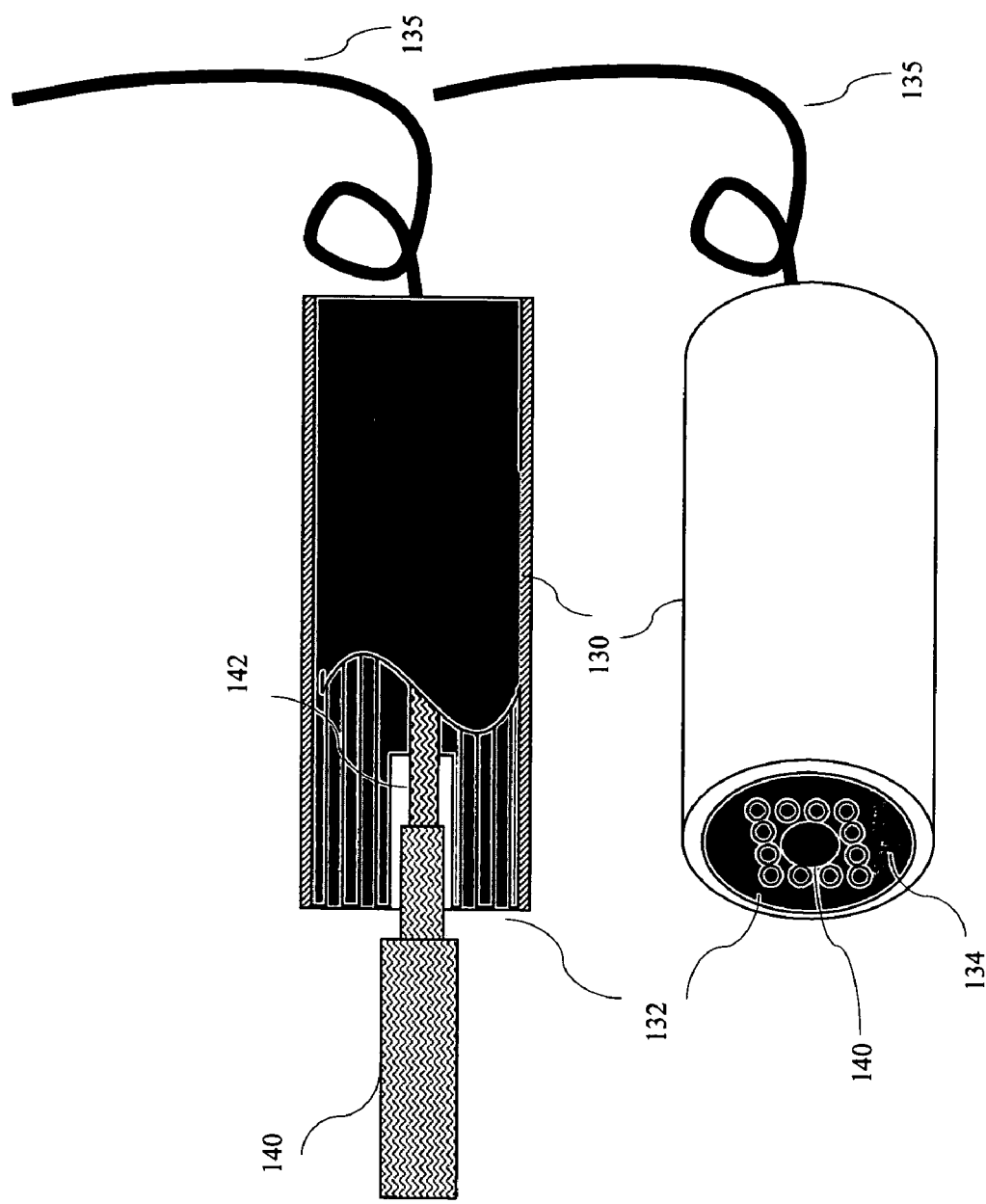
FIG. 21 is a schematic diagram for a multielectrode sensor with a removable rod-shaped built-in large electrode.
Figure 22:
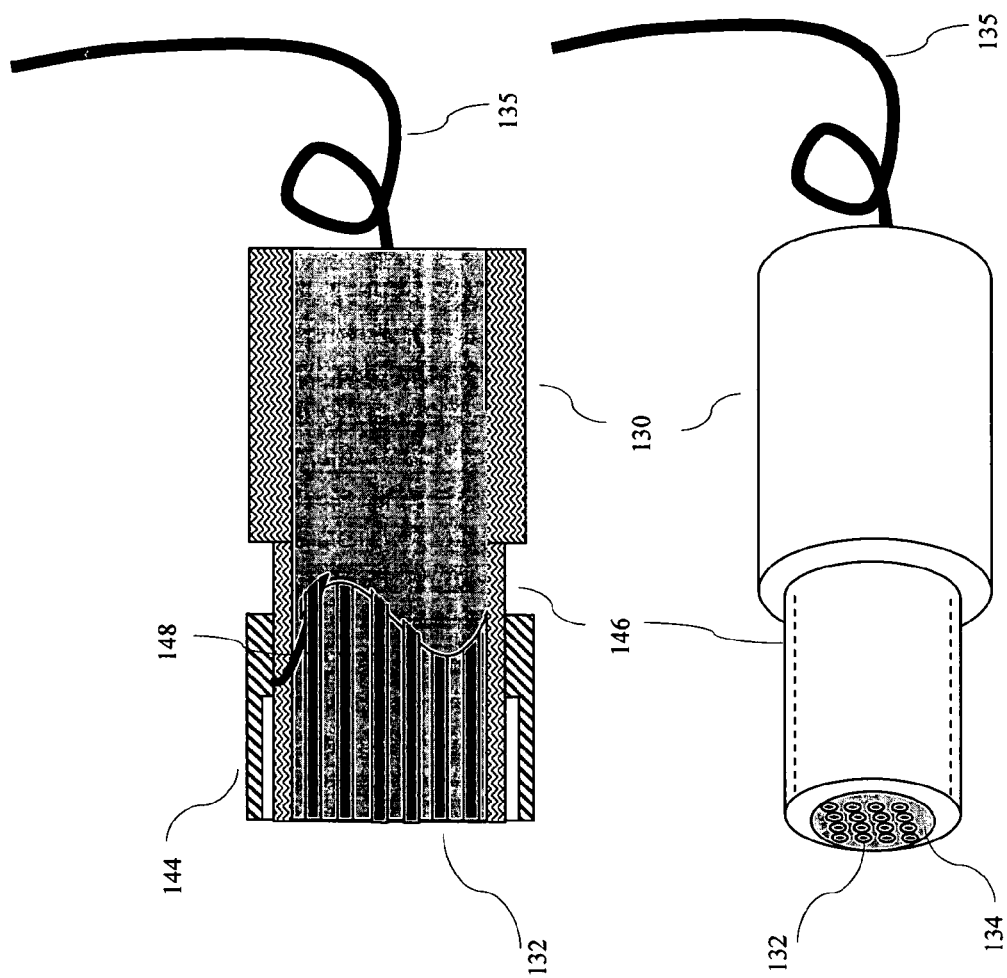
FIG. 22 is a schematic diagram for a multielectrode sensor with a removable tube-shaped built-in large electrode.

FIGS. 21 and 22—Multielectrode Sensors with Built-in Large Electrode for Controlling the Coupling Potential As discussed in the description section for FIGS. 1 through 6, a large electrode 14 made of the same material as the sensing electrodes 132 may be used to stabilize the coupling joint 12 potential, or a large cathode electrode 83 made of a more corrosion-resistant material than the sensing electrodes may be used to raise the potential of the coupling joint 12 potential. FIG. 21 shows a multielectrode sensor with a removable rod-shaped, built-in large electrode 140. The large electrode 140 has a female thread and is connected to the electrical metal connector 142 by means of the thread. The large rod-shaped electrode 140 can be easily removed when the multielectrode sensor is to be polished or re-polished. The removal of the large electrode 140 is also necessary when the multielectrode sensor needs to be cleaned.

FIG. 22 is a slight variation of FIG. 21. In FIG. 22, the large removable electrode 144 is tube-shaped and the probe body 130 is made of a non-conducting material, such as plastic. An embedded metal wire 148 is required for the electrical connection to the large electrode 144.

The probe body 130 can also be made of a material that can serve as the large electrode 14 or 83 in FIGS. 1 through 6. In this case, the probe body needs to be isolated from the metal container or piping if the probe is to be used inside a metal-enclosed system. For instance, the probe may be installed in the metal-enclosed system through a penetration fitting with an electrically non-conducting seal.

ADVANTAGES

From the description above, a number of advantages of the invention become evident:

(a) Connecting the coupling joint of the multielectrode devices to a large electrode using resistance elements, especially the resistance-adjustable elements, or a resistance element and a power source allows the multielectrode device to operate in a more stable manner. This arrangement makes the multielectrode device less affected by the extreme behaviors of one or more electrodes in the device. For example, if one electrode develops a crevice and becomes extremely anodic, all the other electrodes became cathode and are not able to act as the sensing electrodes.

(b) Using a controller or a computer to adjust the coupling resistance so that the potentials of a group of electrodes on a multielectrode device or the potentials of all the electrodes on a sensor are substantially the same, even though the currents through the different electrodes are significantly different from each other, allows the multiple electrodes to better simulate the electrochemical behavior of a one-piece metal in a wide range of environments.

(c) Connecting each of the electrodes of a multielectrode device, through a resistance element or resistance-adjustable resistance element, to the coupling joint in the electronic unit that uses an ammeter or a zero-resistance ammeter eliminates the transient current that may be produced, by switching an electrode from the coupling joint to the ammeter or zero-resistance ammeter (the input impedance of a zero-resistance ammeter is usually not truly zero) and makes the measurement of the coupling currents more reliable and accurate.

(c) An electronic unit that allows a software program to automatically disconnect one or more electrodes from the coupling joint or to lessen their coupling and exclude these electrodes from the measurement if these electrodes give statistically abnormal behaviors during the measurement eliminates the effect of the bad electrodes on the performance of the sensors. This is especially true when one or more of the electrodes are contaminated by a piece of material that has different properties than the sensing electrode.

(d) A software program for multielectrode devices that keeps track of the cumulative charge for each electrode of multielectrode device so that the cumulative corrosion depth or electrodeposition thickness can be calculated based on the cumulative charge from each electrode. For the maximum penetration or deposition calculation, this is more accurate than the calculation based on the maximum corrosion current because the maximum corrosion current may be from one electrode at one time, and from another electrode at another time.

(f) A software program that gives users an option to continue the calculation of cumulative depth or electrodeposition thickness for each electrode, every time the program is started, based on the corroded depth at the time the program was last stopped is useful for the users, because they can continue to keep track of the cumulative corrosion depth or deposition thickness if there is a power failure or if there is a need to temporarily stop the program.

(g) A dual-sensor system, that has a regular sensor as a working sensor for the measurement of both the signal due to corrosion and the baseline signal due to the reaction of the electrochemically active species, and a baseline sensor, which is made of corrosion-resistant material and measures the signal due to the reaction of the electrochemically active species, enables a coupled multielectrode sensor system to be used in an environment containing electrochemically active species.

(h) A dual-sensor system whereby the baseline sensor can be used to measure the biofilm or microbiological activities.

(i) An instrument that has built-in functions to automatically supply a voltage or current to electrochemically clean one or more electrodes of the multielectrode device after they become malfunctioning, so that the sensor can be continuously used.

(j) A multielectrode sensor that has a built-in and removable large electrode for stabilizing or changing the potential of the coupling joint, so that no separate large electrode is required.

OTHER EMBODIMENTS

Although the description above contains many specificities, these details should not be construed as limiting the scope of the invention, but merely as providing illustrations of some of the presently preferred embodiments of this invention. Thus, the scope of the invention should be determined by the appended claims and their legal equivalents, rather than by the examples.

The invention claimed is:

1. An electronic unit for the measurement of the current from each electrode of a multielectrode electrochemical device or corrosion sensor, using a voltmeter or an ammeter, comprising:
   (a) a plurality of electrode wires or channels for connection to the electrodes of a multielectrode device
   (b) a common coupling joint
   (c) a resistance element between each electrode wire and the common coupling joint so that the electrodes of the multielectrode device simulate the electrochemical behavior of one-piece metal
   (d) a cathode connected to the coupling joint through a second resistance element.

2. An electronic unit of claim 1, wherein the first resistance element is comprised of a group of resistors and a switching means, which allow a controller to change the effective value of the resistance element so that the low voltages between the different electrode wires and the coupling joint are substantially similar for the multielectrode device to simulate the electrochemical behavior of a one-piece metal in a wide range of environments.

3. An electronic unit of claim 1, wherein the second resistance element is comprised of a group of resistors and a switching means, which allows a controller to change the effective value of the second resistance element, so that the potential at the coupling joint is changed to a designed value.

4. An electronic unit of claim 1, wherein the second resistance element is comprised of a group of resistors and a switching means, which allow a controller to change the effective resistance value of the second resistance element, and a power source is added between the second resistance element and the cathode, so that the potential at the coupling joint can be varied in a wide range.

5. An electronic unit of claim 2, wherein the second resistance element is comprised of a group of resistors and a switching means, which allow a controller to change the effective value of the second resistance element, so that the potential at the coupling joint is changed to a designed value.

6. An electronic unit of claim 1, wherein the first resistance element is comprised of a group of resistors and a switching means, which allow a controller to disconnect the electrode wire from the coupling joint, so that the electrode connected to the electrode wire will not affect the behavior of other electrodes of the multielectrode device or the open-circuit potential of the electrode connected to the electrode wire can be measured.

7. An electronic unit of claim 1, wherein the first resistance element is comprised of a group of resistors and a switching means, which allows a controller to significantly increase the effective resistance value, so that the electrode connected to the electrode wire will less affect the behavior of other electrodes of the multielectrode device.

8. An integrated electronic system that consists of two or more electronic units of claim 1, which gives a user the flexibility to use each of the electronic units for one multielectrode device with smaller number of electrodes, to use two or more of the electronic units for one multielectrode device with a larger number of electrodes, or to use the integrated electronic system for two or more independent multielectrode devices simultaneously.

9. An electronic unit for the measurement of the current from each electrode of a multielectrode electrochemical device or corrosion sensor, comprising:

(a) a plurality of electrode wires or channels for connection to the electrodes of a multielectrode device (b) a common coupling joint (c) a resistance element between each electrode wire and the common coupling joint so that the electrodes of the multielectrode device simulate the electrochemical behavior of one-piece metal (d) an ammeter or a zero-resistance-ammeter for measuring the current through each electrode connected to the electrode wire wherein said resistance element is made of a group of resistors and a switching means, so that the effective resistance value can be varied by an electronic controller or a computer.

10. An electronic unit of claim 9, wherein said effective resistance value of each resistance element can be varied independently in a large range up to infinity by an electronic controller or a computer.

\* \* \* \* \*